US012108698B2

(12) United States Patent
Barrick et al.

(10) Patent No.: US 12,108,698 B2
(45) Date of Patent: Oct. 8, 2024

(54) AUTOMATED SEED PLANTING AND EVALUATION

(71) Applicant: Monsanto Technology LLC, St. Louis, MO (US)

(72) Inventors: Adam M. Barrick, St. Louis, MO (US); Eric L. Borrowman, St. Peters, MO (US); Jarrett R. Ceglinski, Damiansville, IL (US); Jerry Christopher, Collinsville, IL (US); Joshua Allen Crews, Lake Saint Louis, MO (US); Daniel Dillard, Labadie, MO (US); Timothy P. Garvin, Geneva, IL (US); Charles K. Johnson, Sycamore, IL (US); Jeffrey L. Kohne, Kirkwood, MO (US); Jason T. Mitchell, St. Charles, MO (US); Jeffrey S. Morris, St. Charles, MO (US); Ralph E. Nothdurft, Affton, MO (US); Payman Rassoolkhani, Maryland Heights, MO (US); Christian A. Saia, St. Louis, MO (US)

(73) Assignee: MONSANTO TECHNOLOGY LLC, Saint Louis, MO (US)

( * ) Notice: Subject to any disclaimer, the term of this patent is extended or adjusted under 35 U.S.C. 154(b) by 1224 days.

(21) Appl. No.: 16/458,754

(22) Filed: Jul. 1, 2019

(65) Prior Publication Data
US 2020/0000007 A1     Jan. 2, 2020

Related U.S. Application Data

(60) Provisional application No. 62/692,853, filed on Jul. 1, 2018.

(51) Int. Cl.
*A01C 1/02*     (2006.01)
*A01C 1/04*     (2006.01)
(Continued)

(52) U.S. Cl.
CPC .............. *A01C 1/025* (2013.01); *A01C 1/04* (2013.01); *G01N 35/04* (2013.01); *G01N 33/0098* (2013.01); *G01N 2035/0496* (2013.01)

(58) Field of Classification Search
CPC .. A01C 1/00; A01C 1/02; A01C 1/025; A01C 1/04; A01C 2001/048
(Continued)

(56) References Cited

U.S. PATENT DOCUMENTS

| 4,221,175 A | 9/1980 | Van Wingerden et al. |
| 4,325,200 A * | 4/1982 | Ovarnstrom ........... A01G 9/081 |
| | | 47/1.01 R |

(Continued)

FOREIGN PATENT DOCUMENTS

| CN | 105917910 A | 9/2016 |
| JP | H08 154427 A | 6/1996 |

(Continued)

OTHER PUBLICATIONS

Maloney, B., Keys to Success for Germination of Triploid Watermelon Seeds, Jan. 2001, Vegetable Production & Marketing News, Dainello, Ed., Extension Horticulture, Texam Agricultural Extension Service, The Texas A&M University System, College Station, TX, Sep. 12, 2019, Novartis, https://aggie-horticulture.tamu.edu/extension/newsletters/vpmnews/jan01/art3jan.html, 2 pages.

(Continued)

*Primary Examiner* — David J Parsley
(74) *Attorney, Agent, or Firm* — Harness, Dickey & Pierce, P.L.C.

(57) ABSTRACT

Provided herein are systems and methods for the automation of seed planting and analysis comprising automated planting of the seeds, germination, and analysis. The methods generally comprise conveying containers containing seeds to an
(Continued)

automated seed planting station, wherein each container includes a machine-readable tag, planting at least some of the seeds in the container onto respective planting trays, wherein each planting tray includes a machine-readable tag, allowing the seeds to germinate, and analyzing the germinated seeds. The systems generally comprise a seed planting system and a planting verification and correction system. Also provided herein are backlit templates comprising a light source and a power interface configured to connect to a power source to power the light source.

18 Claims, 40 Drawing Sheets

(51) Int. Cl.
*G01N 35/04* (2006.01)
*G01N 33/00* (2006.01)

(58) Field of Classification Search
USPC .................. 47/14, 57.6, 58.1 R, 58.1 SE
See application file for complete search history.

(56) References Cited

U.S. PATENT DOCUMENTS

| | | |
|---|---|---|
| 7,998,669 B2 | 8/2011 | Deppermann et al. |
| 8,189,901 B2 * | 5/2012 | Modiano .................. B07C 5/00 47/14 |
| 8,833,565 B2 | 9/2014 | Becker et al. |
| 9,578,797 B2 * | 2/2017 | Deppermann ......... A01C 1/025 |
| 2003/0106258 A1 | 6/2003 | Keller et al. |
| 2010/0047801 A1 * | 2/2010 | Cope ........................ A01C 1/00 435/6.12 |
| 2015/0212058 A1 | 7/2015 | Koutsky et al. |
| 2016/0313220 A1 | 10/2016 | Deppermann et al. |
| 2016/0318074 A1 | 11/2016 | Deppermann |
| 2018/0110186 A1 | 4/2018 | Bovee |

FOREIGN PATENT DOCUMENTS

| | | |
|---|---|---|
| KR | 200214873 Y1 | 2/2001 |
| RU | 110897 U1 | 12/2011 |
| RU | 2612213 C2 | 3/2017 |
| WO | WO 88/03357 A1 | 5/1988 |
| WO | WO2011/119402 A1 | 9/2011 |
| WO | 2016/200825 A1 | 12/2016 |

OTHER PUBLICATIONS

Filho, J.M., "Seed Vigor Testing: An Overview of the Past, Present and Future Perspective," Jul./Aug. 2015, Sci Agric (Piracicaba, Braz), 72/4, www.scielo.br/scielo.php?script=sci_arttext&pid=S0103-90162015000400363, 17 pages.

* cited by examiner

AUTOMATED SEED PLANTING AND EVALUATION

FIELD OF THE DISCLOSURE

The present disclosure generally relates to a system and method for automated seed planting and evaluation, such as in a lab-type setting for testing seeds.

BACKGROUND OF THE DISCLOSURE

Conventionally, seeds are tested in a lab-type setting to determine, for example, seed viability and seed vigor. Such seed testing is typically performed manually, making it labor intensive and prone to human error.

SUMMARY OF THE DISCLOSURE

In one aspect, a system and method for automated seed planting and evaluation for testing seeds is described. At least a majority of the system and method is automated, making the testing of seeds less labor intensive and less likely to be prone to human error.

In another aspect, the present invention is directed to a seed planting template for a planting tray comprising a template upper portion defining individual wells configured to hold seeds, a light source below the wells, a template bottom portion defining openings, and a power interface configured to connect a power source to power the light source. The template has a placement configuration, wherein the wells of the template upper portion are not aligned with the openings of the template bottom portion and the wells are configured to be backlit by the light source. The template also has a planting configuration, wherein the wells of the template upper portion are aligned with the openings of the template bottom portion to allow seeds in the wells to fall through the openings of the template bottom portion and onto the planting tray.

BRIEF DESCRIPTION OF THE DRAWINGS

Corresponding reference characters indicate corresponding parts throughout the drawings.

DETAILED DESCRIPTION OF THE DISCLOSURE

Figure 1:
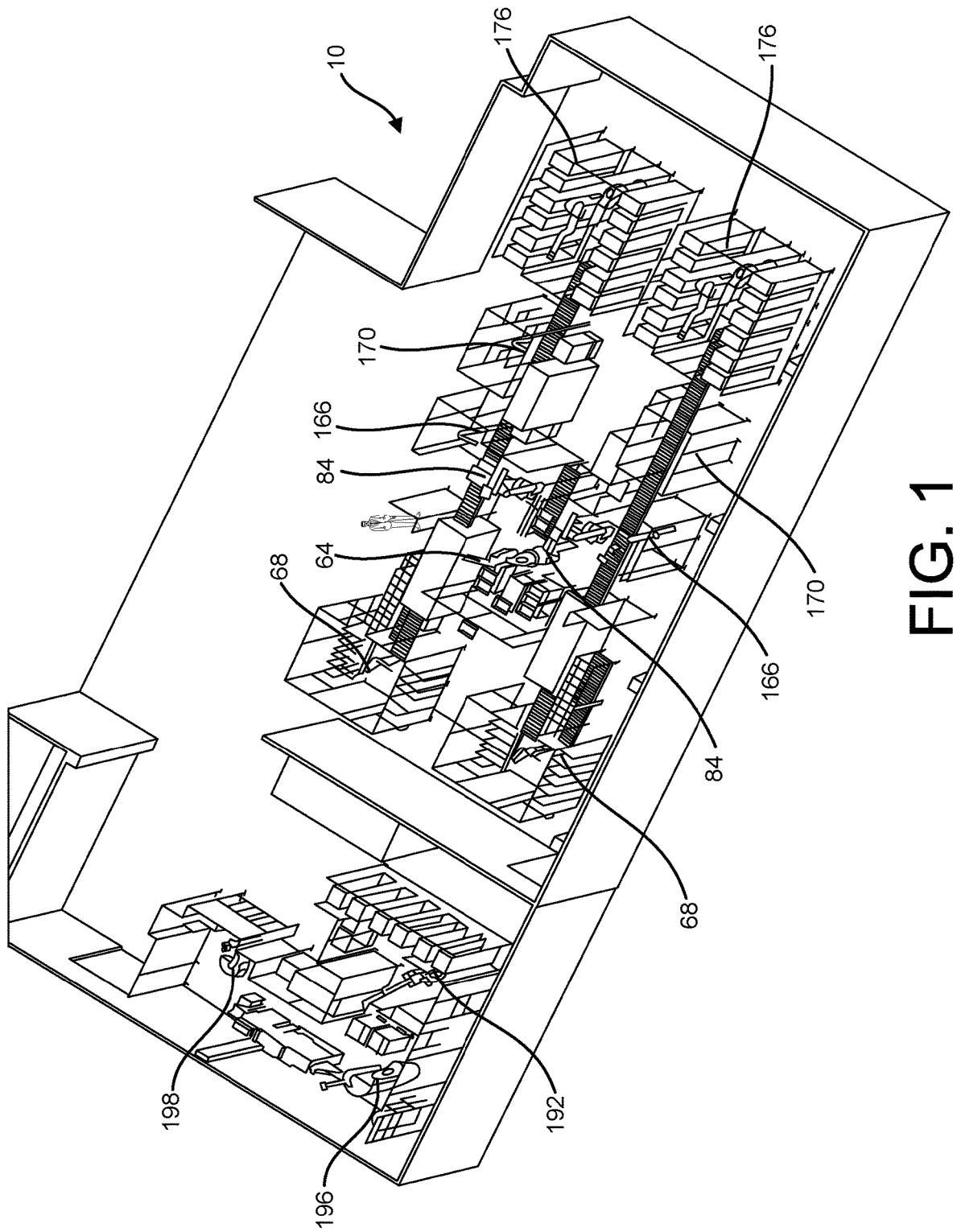
FIG. 1 is an image of an embodiment of the seed testing system of the present disclosure.

Referring to FIG. 1, an automated seed testing system 10 constructed according to the teachings of the present disclosure is depicted. The seed testing system 10 may be located in a controlled, lab-type setting within a building. In general and as described in more detail below, the seed testing system includes a plurality of robots (or other automated device or system) capable of performing different tasks, as described below, a seed splitting system, a conveyor system including sensors, paper dispense system, agar mixing and batch dispenser, cooling tunnels for temperature control, automatic indexers for cart placement, seed placement and accuracy counter, imaging and evaluation station, and substrate mixing and placing apparatuses. One or more of the components are operated by one or more controllers (e.g., programmable logic controller including a processor and memory). If more than one controller is implemented, the controllers may be in communication with one another. In one or more embodiments, one or more of the robots described below may be replaced by another type of automated device or system suitable for performing the described function of the particular robot.

Figure 2:
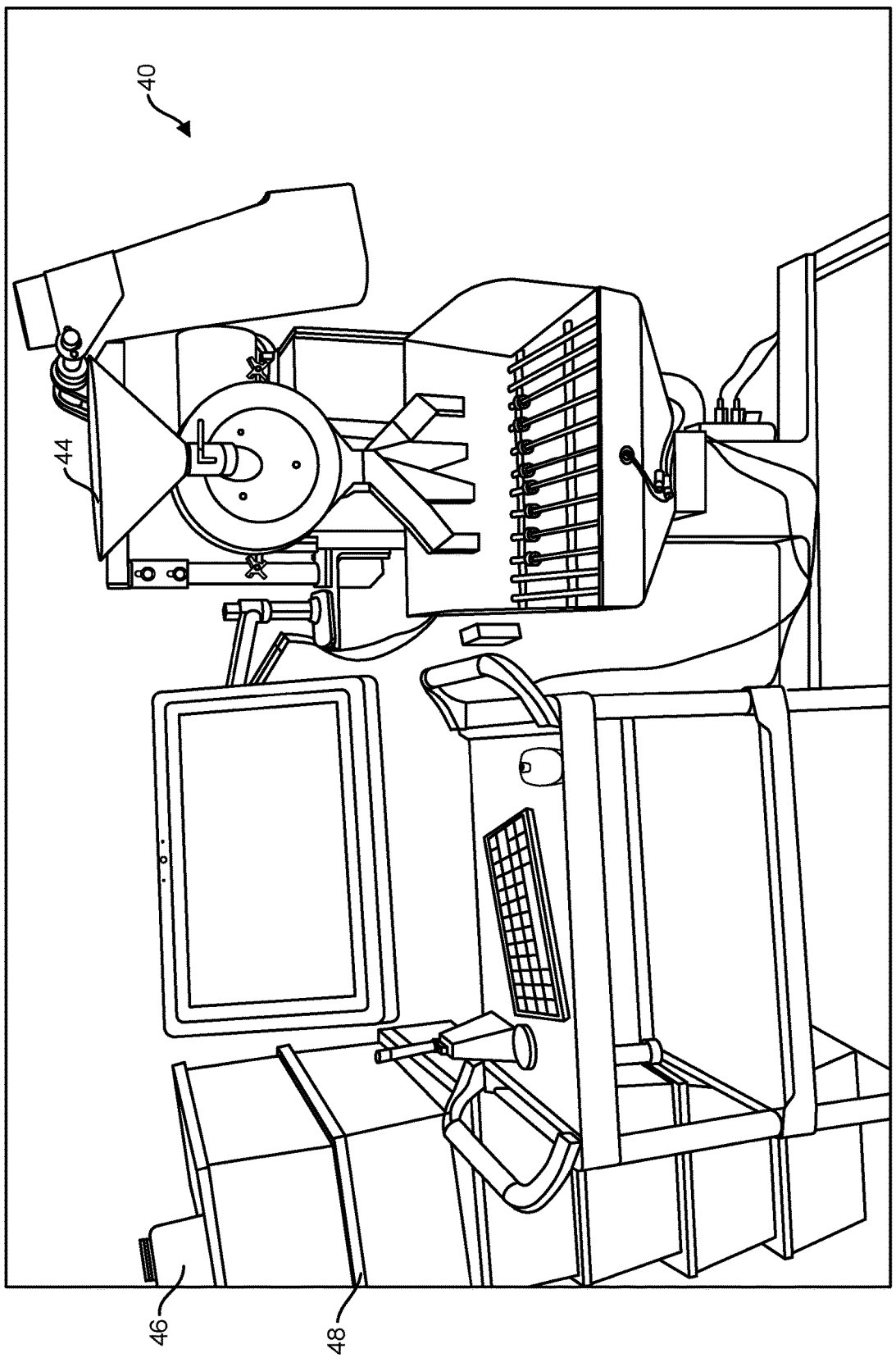
FIG. 2 is an image of a seed splitter system.

Referring to FIG. 2, before being received at the illustrated seed testing system 10, production seed samples are received at a seed splitter system 40 where batch IDs (e.g., bar codes) associated with the seed samples are scanned. The sample seeds are placed into a hopper 44 of the system, and the seed splitter system separates the seeds into up to four bottles 46 (e.g., containers). This process can be done manually by an operator putting seed into the seed splitter system or by automated means. The seeds in each bottle 46 will undergo a separate test at the seed testing system 10. Each of the sample bottles 46 are affixed with an RFID (radio-frequency identification) tag or other machine-readable tag or label. The splitter system 40 writes the inspection lot data to the tag as machine-readable information. It also sends other data about the sample to a control database of the seed testing system 10. The machine-readable tag is configured to associate the bottle (e.g., container) with information stored in a database relating to the seeds contained in the bottle (e.g., container). As described herein, the machine-readable tag of the bottle 46 is scanned at discrete locations during the processes described herein. Seed sample bottles 46 are loaded into totes 48 and delivered to the seed testing system 10. The totes 48 are affixed with an RFID tag (or other machine readable tag or label) that includes, for example, machine-readable information regarding the contents (e.g., seed samples in the bottles 46) of the totes 48 and the locations of the individual bottles 46 within the totes 48. In one or more embodiments, the seed splitter system 40 may be incorporated into the seed testing system 10.

Figure 3:
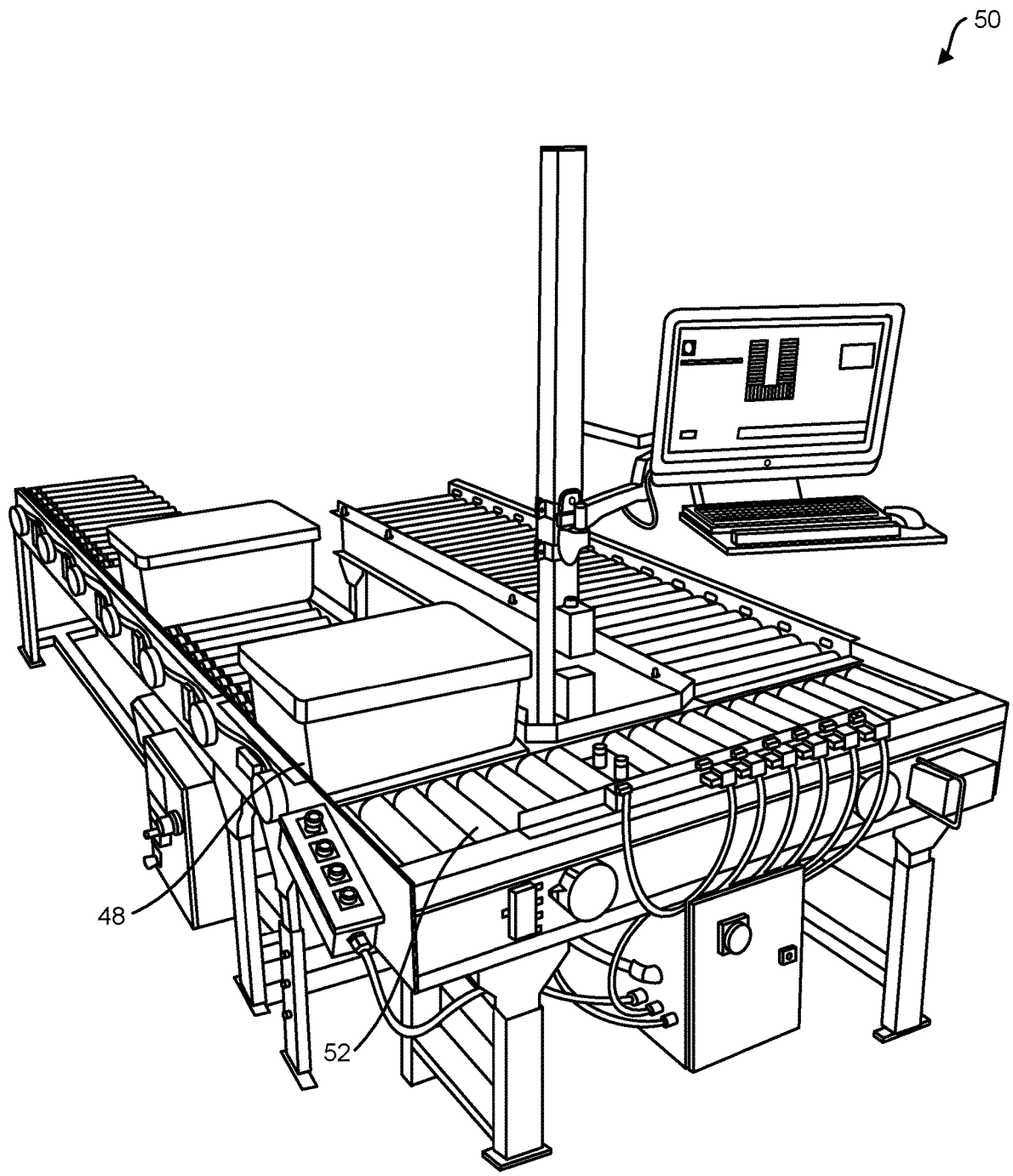
FIG. 3 is an image of a receiving system.

Referring to FIG. 3, the filled totes 48 including the bottled sample seeds are delivered to a receiving system 50. The RFID tags of the totes 48 and the bottles 46 in the totes 48 are scanned by sensors of the receiving system 50 as they move along a receiving conveyor 52 of the receiving system. The seeds in the individual bottles 46 are identified by test type (e.g., RET (Radicle Emergence Testing on an agar platform) and WG (warm germ testing on specialized media)), inventoried and electronically received into the controller of the seed test system 10. The skilled person will understand that this process can encompass other seed testing systems, particularly seed quality testing that involves imaging, for example seed morphological characters, including: internal and external cracks, embryo size and overall appearance of the seed batch. The totes 48 are conveyed out of the receiving system 50 via the conveyor 52 and arranged by test type, for example, either manually or automatically. In the illustrated embodiment, during operation of the seed testing system 10, the totes 48 including the bottles 46 are moved manually to a planting line of the seed testing system 10. In other embodiments, the totes 48 may be delivered by an automated process.

Figure 4:
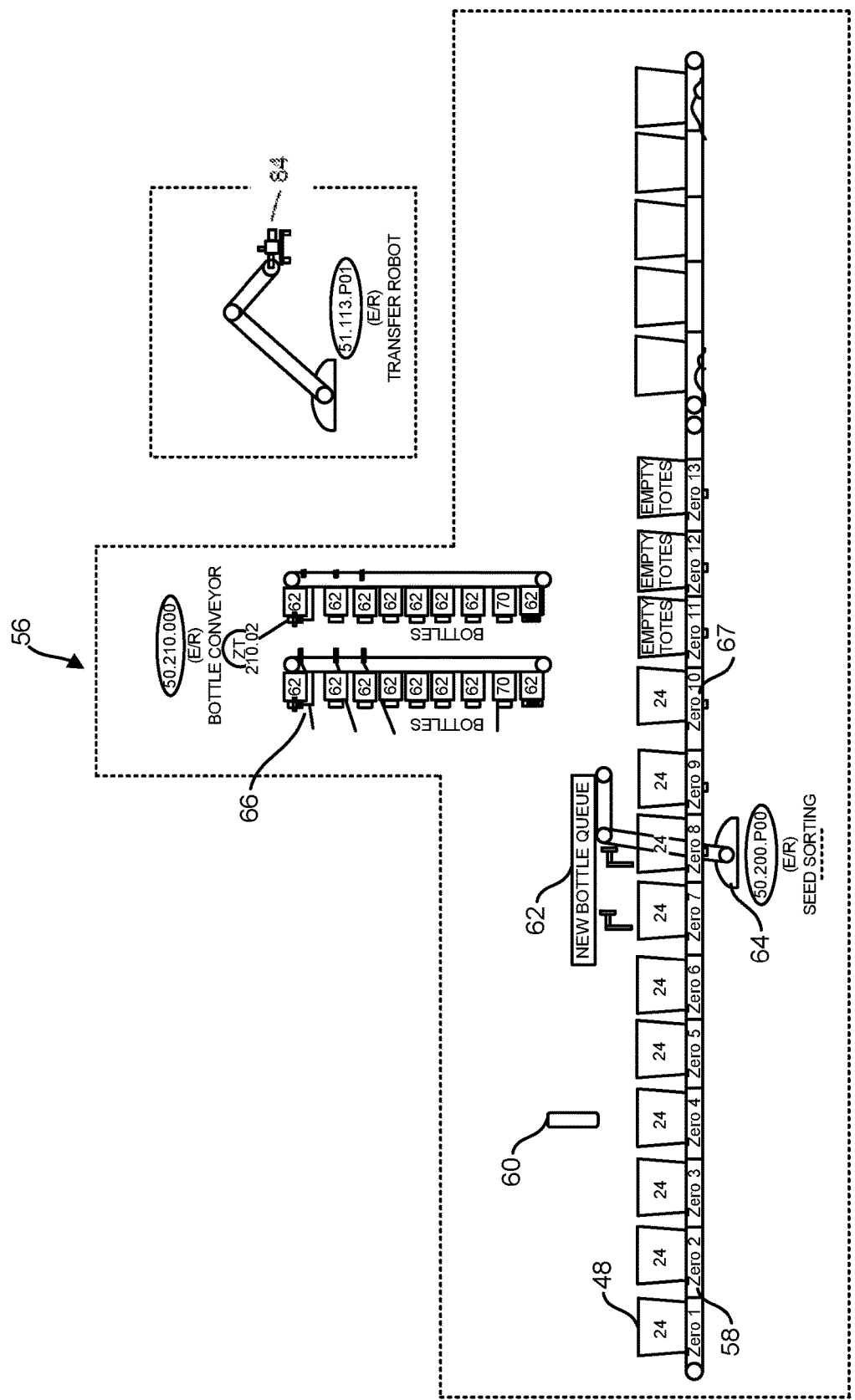
FIG. 4 is an image of a seed sorting system.
Figure 5:
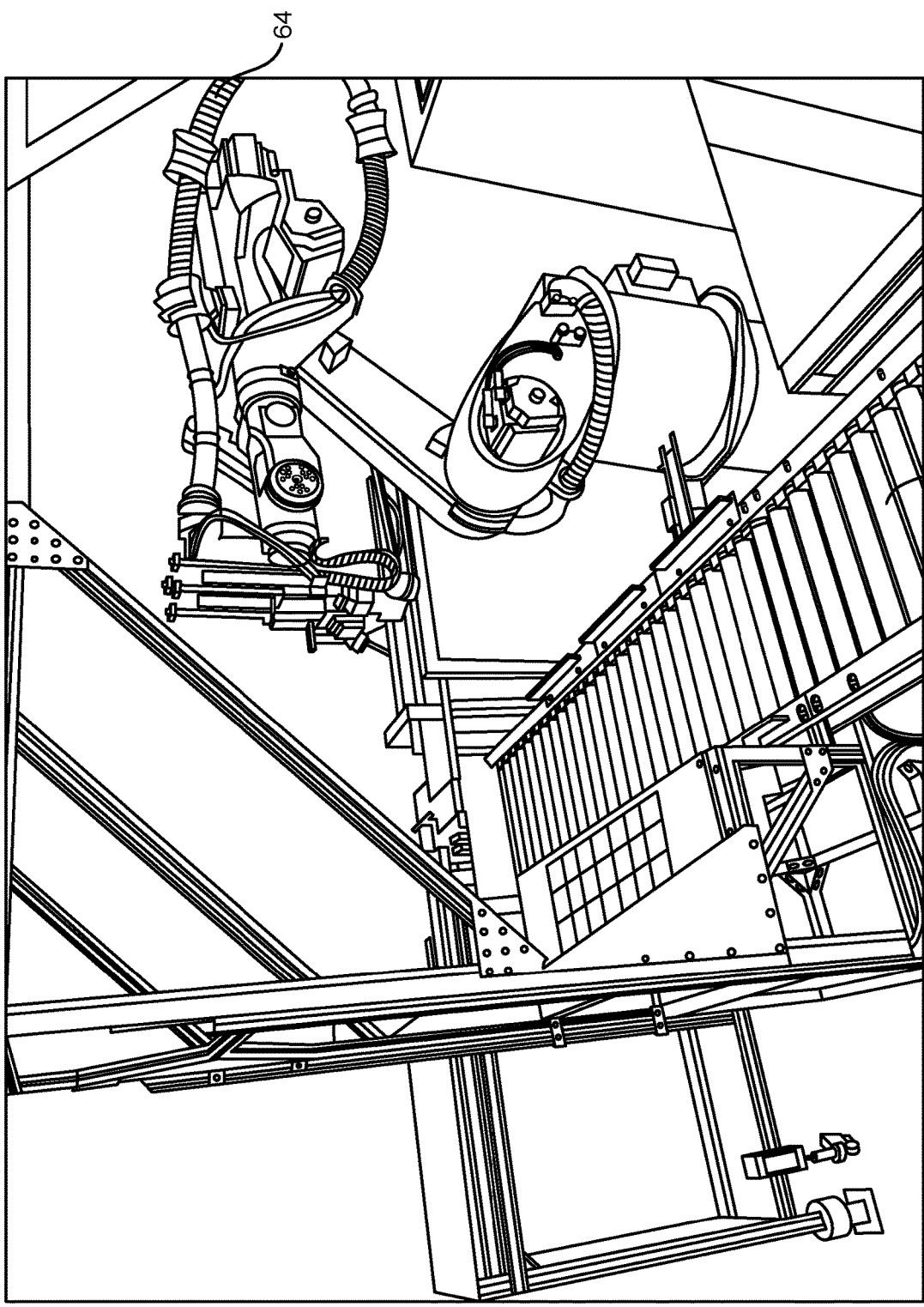
FIG. 5 is an image of a sorting conveyor and queuing robot of the present disclosure.

Referring to FIGS. 4 and 5, at a seed sorting system 56, the totes 48 are placed on to a sorting conveyor 58 and the lid is opened, such as manually or through the use of a robot or other machine. The sorting conveyor 58 delivers the totes through a scanning station 60. At the scanning station 60 the tote 48 and the contents RFID tags are read by sensor(s). The locations of each bottle 46 within the totes 48 are sent to the controller (e.g., programmable logic controller (PLC)). Using the tote data read from the RFID tags, the bottles 46 are sorted into plantable pairs (samples with the same testing requirement and the same seeder settings) within a database (DB). Using the plantable pairs data in the database, at a queueing station 62 along the sorting conveyor 58 the controller communicates to a queueing robot 64 to pick up the bottles 46 by pairs, place them on a bottle-queueing conveyor 66 and remove the lids of the bottles 46. If there are bottles 46 in the totes 48 that do not have available pairs in the queueing station 62, the non-paired bottles may be moved by the queueing robot 64 to a buffer or holding station (not pictured) (if there is also not a bottle in the holding station that can be paired with the non-paired bottle). The locations of the non-paired bottles within the holding station are stored in the database. The database pairs available non-paired bottles at the holding station with bottles 46 in the totes 48 at the queueing station 62. If applicable, the controller communicates to the robot to pair and queue the non-paired bottle 46 and the bottle 46 in the tote 48. The queueing robot 64 will continue to unload the bottles 46 from the tote 48 until the tote is empty or the bottle-queueing conveyor 66 is full. Once the tote 48 is empty, the tote 48 will index forward to the next zone 67 on the conveyor 58 and be reloaded with lids and empty bottles. The next tote 48 will index into the queueing station 62 and the process repeats. In the illustrated embodiment, the queueing robot 64 can pick from 3 totes 48 within the queueing station 62 and the holding station to create the plantable pairs.

Figure 6:
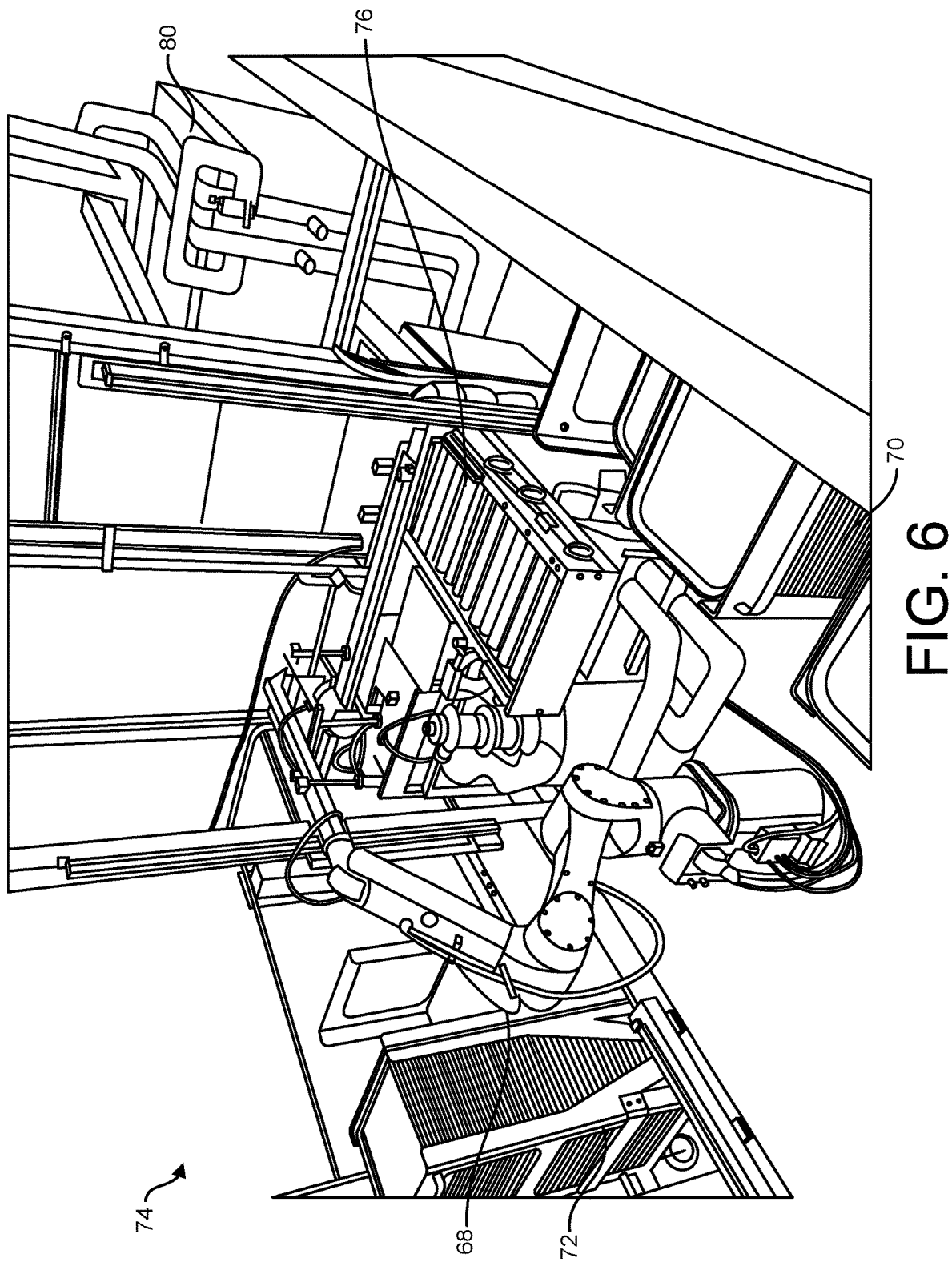
FIG. 6 is an image of a tray conveyor and tray robot with radicle emergence testing and warm germ tray carts.
Figure 7:
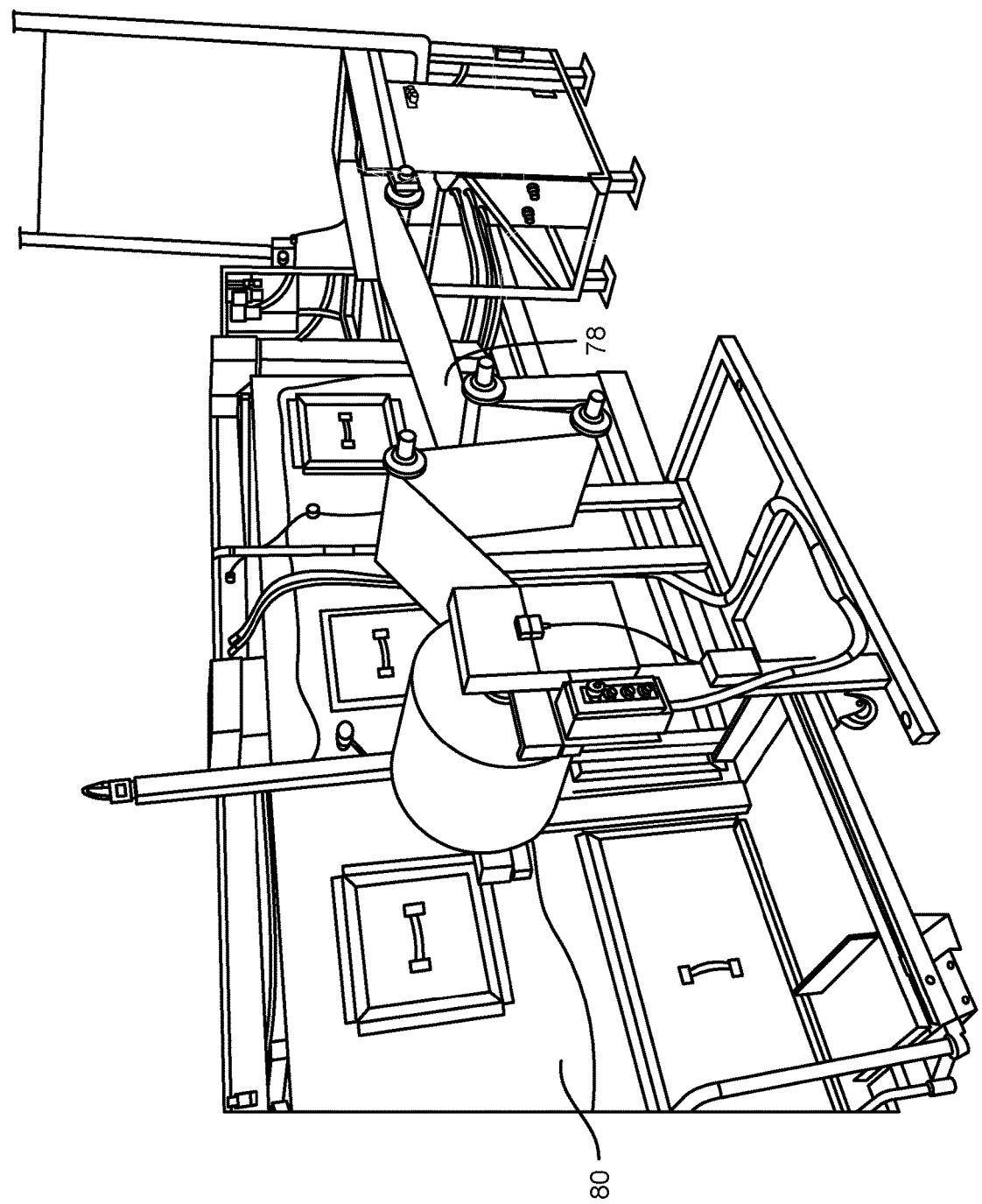
FIG. 7 is an image of a cooling tunnel with paper sheeter.

Referring to FIGS. 6 and 7, at the same time the bottle pairs are loaded on to the bottle-queueing conveyor 66, a tray type list is created in the database. This list is used by the controller (e.g., PLC) to command a tray robot(s) 68 (e.g, an automated tray selection apparatus) to the correct planting tray type cart 70, 72 at a tray-loading station 74 and deliver the correct type and quantity of planting trays to a tray conveyor. In the illustrated embodiment, there are two types of trays: RET trays 72 and warm germ (WG) trays 70. The tray robot 68 will pick the correct tray type and quantity to begin the planting process. The RET trays 72 require agar gel on a transparent, plastic tray. The illustrated agar trays are separated into two sections for a total of 100 sample seeds on each side, although it may hold less than or more than this amount of seeds. The WG trays 70 can be an opaque tray (e.g., cafeteria style) with a paper substrate (e.g., carbonless copy paper, CCP) on the tray. In one example, 200 seeds may be placed on the paper substrate on the WG tray at a time, although the tray 70 may hold less than or more than this amount of seeds.

When instructed by the controller, the tray robot 68 picks up and places the RET tray 72 on the tray conveyor 76. On the conveyor 76, an RFID tag attached to the RET tray 72 is read by a sensor and inputted to the controller to confirm it is an RET tray 72. The tray RET ID is inputted to a Tray Table in the database. After confirmation, an agar liquid dispenser, controlled by the controller, dispenses agar liquid from an agar batch system onto the RET tray as it moves along the conveyor. The temperature of the agar liquid is monitored by the controller so it is suitable for flowing onto the tray. The controller may also monitor the amount of agar present in the batch.

When instructed by the controller, the tray robot 68 picks up and places the WG tray 70 on the tray conveyor. On the conveyor, an RFID tag attached to the WG tray 70 is read by a sensor and inputted to the controller to confirm it is a WG tray 70. The tray WG ID is inputted to the Tray Table in the database. After confirmation, an automated paper sheeter 78, controlled by the controller, cuts a sheet of paper (e.g., CCP) off a large roll and places it on the WG tray 70 as it passes along the conveyor 76. The machine-readable tag of the tray 70, 72 is configured to associate the tray 70, 72 with the information stored in the database relating to the seed planted on the tray 70, 72. As described herein, the machine-readable tag of the tray 70, 72 is scanned at discrete locations during the processes described herein.

Figure 8:
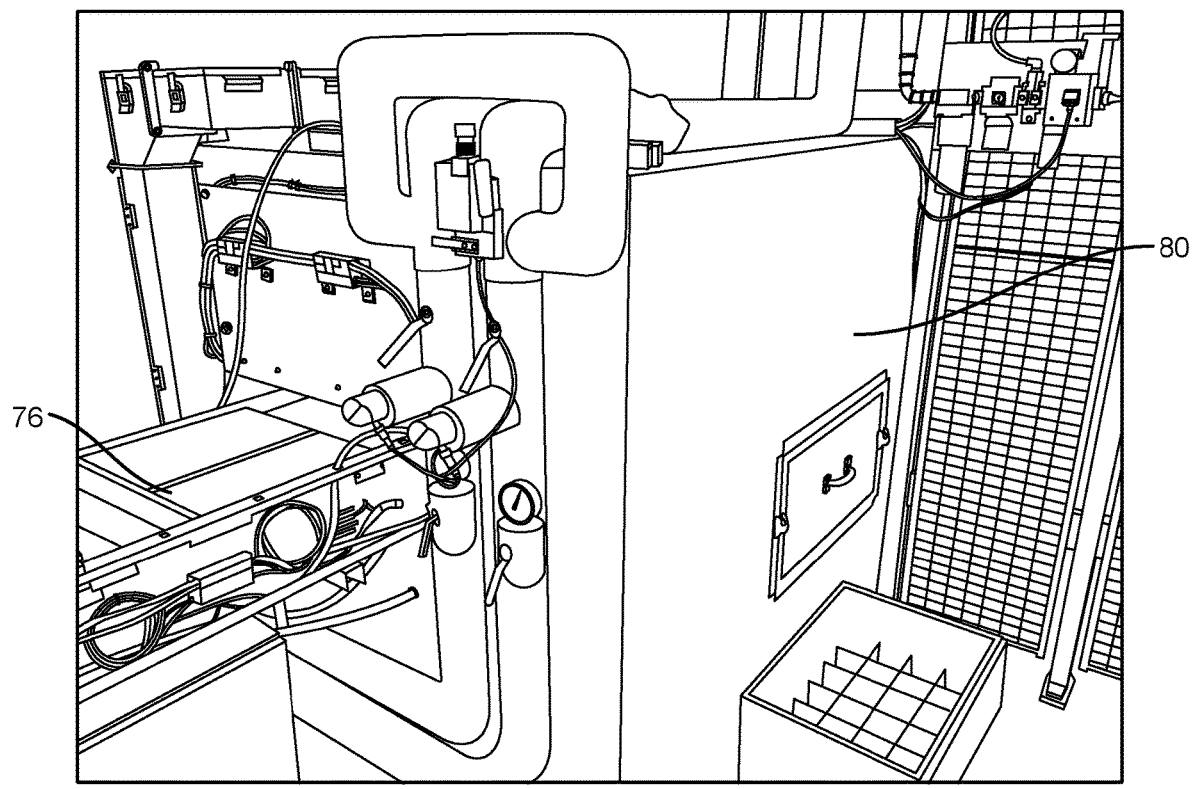
FIG. 8 is a second perspective of a cooling tunnel with a tray conveyor.

Referring to FIGS. 7 and 8, the trays continue to advance along the conveyor to a cooling tunnel 80. The cooling tunnel 80 is an enclosed, temperature controlled system that cools the RET trays 72 as they pass through the controlled environment. (The WG trays 70 also pass through the cooling tunnel 80 but the cooling tunnel 80 is not operated during this time. Alternatively, the cooling tunnel 80 may remain on. This system lowers the temperature of the liquid agar to its gelling temperature. The temperature of the agar gel is preferably lower than 28° C. when exiting the cooling tunnel 80 on the conveyor 76. The liquid agar on the RET tray 72 can be cooled to the working temperature in a reduced time and in less space than room temperature cooling. The temperature of the cooling tunnel 80 is monitored by the controller. After exiting the cooling tunnel 80, the RFID tags of the trays 70, 72 exiting the cooling tunnel 80 are read by a sensor to determine if it is the correct tray type. For example, in the case an error is detected, the system can correct the error or notify an operator to correct the error. The controller compares the test type to the tray type requirements from the database. The inspection lots assigned to the seeds are now assigned to the tray ID in the Tray Table in the database. After passing through the cooling tunnel 80, the paper on the WG trays 70 are wetted by overhead spray nozzles (the RET trays 72 are not wetted). The temperature of the water being sprayed on the WG trays 70 may be monitored and adjusted.

Figure 9:
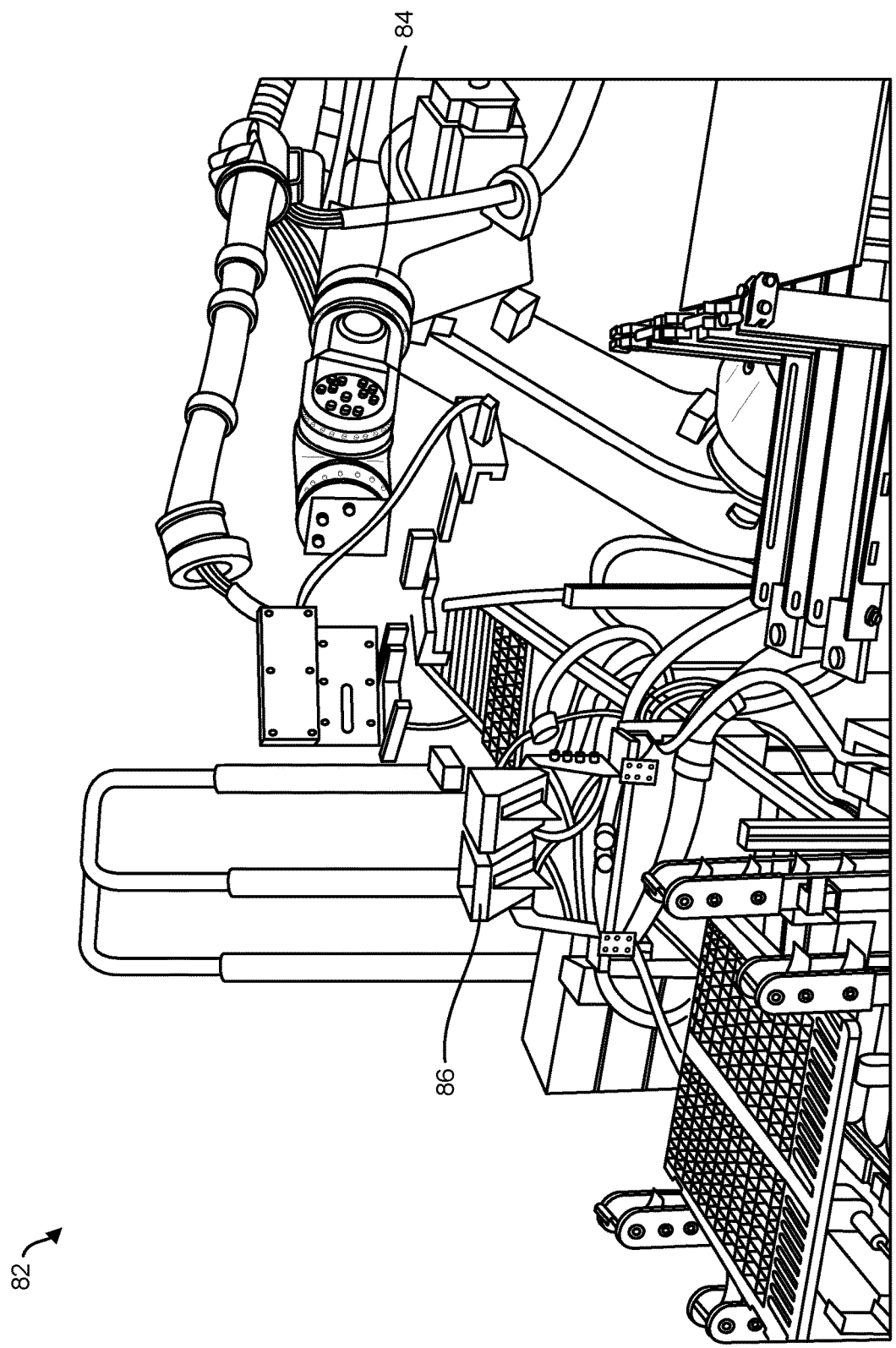
FIG. 9 is an image of a seed planting station.

Referring to FIGS. 9 and 10, the sample seeds are planted on the desired tray at a seed planting station 82. The trays 70, 72 are delivered to the seed planting station 82 via the tray conveyor 76. The seed planting station 82 includes a transfer robot 84 and a seed placement system 86 or seed planter. In one or more embodiments, the seed planting station can be a different configuration and/or include other components suitable for planting the seeds on the trays 70, 72 or other suitable media. The transfer robot 84 picks up the bottles 46 from the queueing conveyor 66 and delivers the bottles 46 to the seed placement system 86 (e.g., a pair of hoppers). The robot 84 takes the emptied bottles 46 to an empty tote 48 for reuse. The illustrated seed placement system 86 is a modified, automated cylinder seeder. In general, the modified, automated cylinder seeder includes (a) seed hoppers, (b) automated seed removal systems for removal of excess seed, (c) automated control valves in place of manual air regulators, (d) a collection hood and automatic conveyance of excess seed to a waste holding drum in place of excess seed collection pan, (e) a seed sample gathering port to collect seed sample used in correcting seed count, (f) a shortened conveyor belt with increased control (e.g., better traction) of the tray, (g) automated servo actuated seed supply tray tilt, (h) a seed pan vibration amplitude sensor (e.g., feedback sensor), and/or (i) a controller for seed pan vibration amplitude. The modified, automated cylinder seeder can be used in fully automatic processes or semi-automatic processes. The modified seed cylinder confers several advantages, including increased throughput, continuity of data, and reduced human corruption of data. In one or more embodiments, the seed placement system may be of a different configuration and/or a different type of automated seeder or device suitable for use in placing or planting the seeds on the trays 70, 72 or other suitable media.

A testing tray 70, 72 is conveyed into position under the cylinder seeder 86 and the cylinder of the seeder starts turning. Small holes in the cylinder allow vacuum to pull seeds to the cylinder face. As the cylinder rotates and the set of holes reach the bottom of the cylinder the vacuum is shut off and the seeds drop on to the tray 70, 72 through a template 90 that regulates the placement on the tray 70, 72. The cylinder may have 3 or more rows of holes and plants 20 seeds per row. When not handling seed bottles 46, the transfer robot 84 removes the seeding template 90 from the tray 70, 72 after planting and returns it to the template placing station 92. In various embodiments, the template placing station 92 is a lowering system (e.g., a lowering elevator or other automated device) that moves the templates 90 downwardly to the tray 70, 72, ideally in a gentle and controlled manner in order to prevent damage to the template 90 while also providing uniform placement of the template 90 onto the testing tray 70, 72. In some embodiments, the template 90 comprises a uniform background in order to aid with seed count.

Figure 10A:
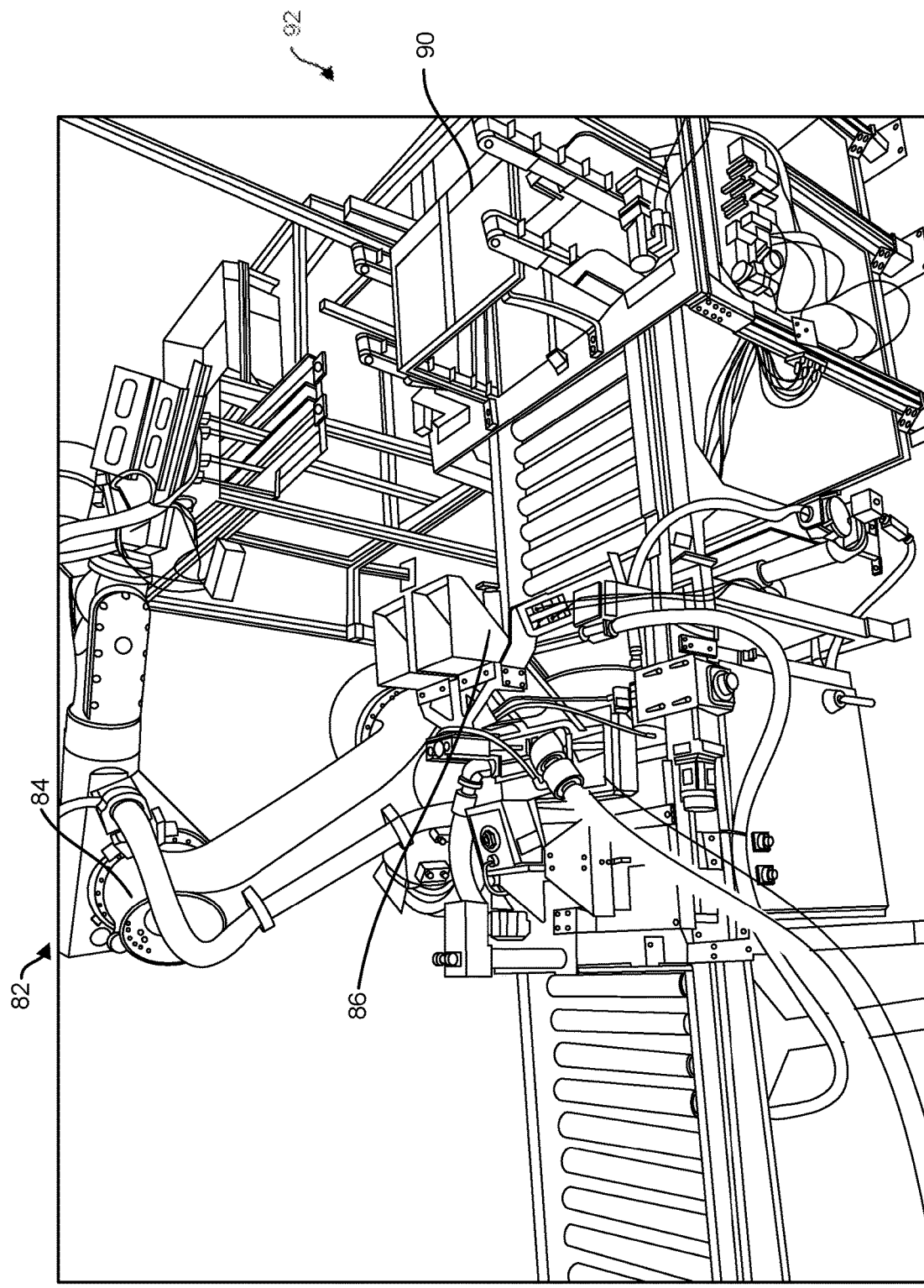
FIG. 10A is a second perspective of a seed planting station.
Figure 10B:
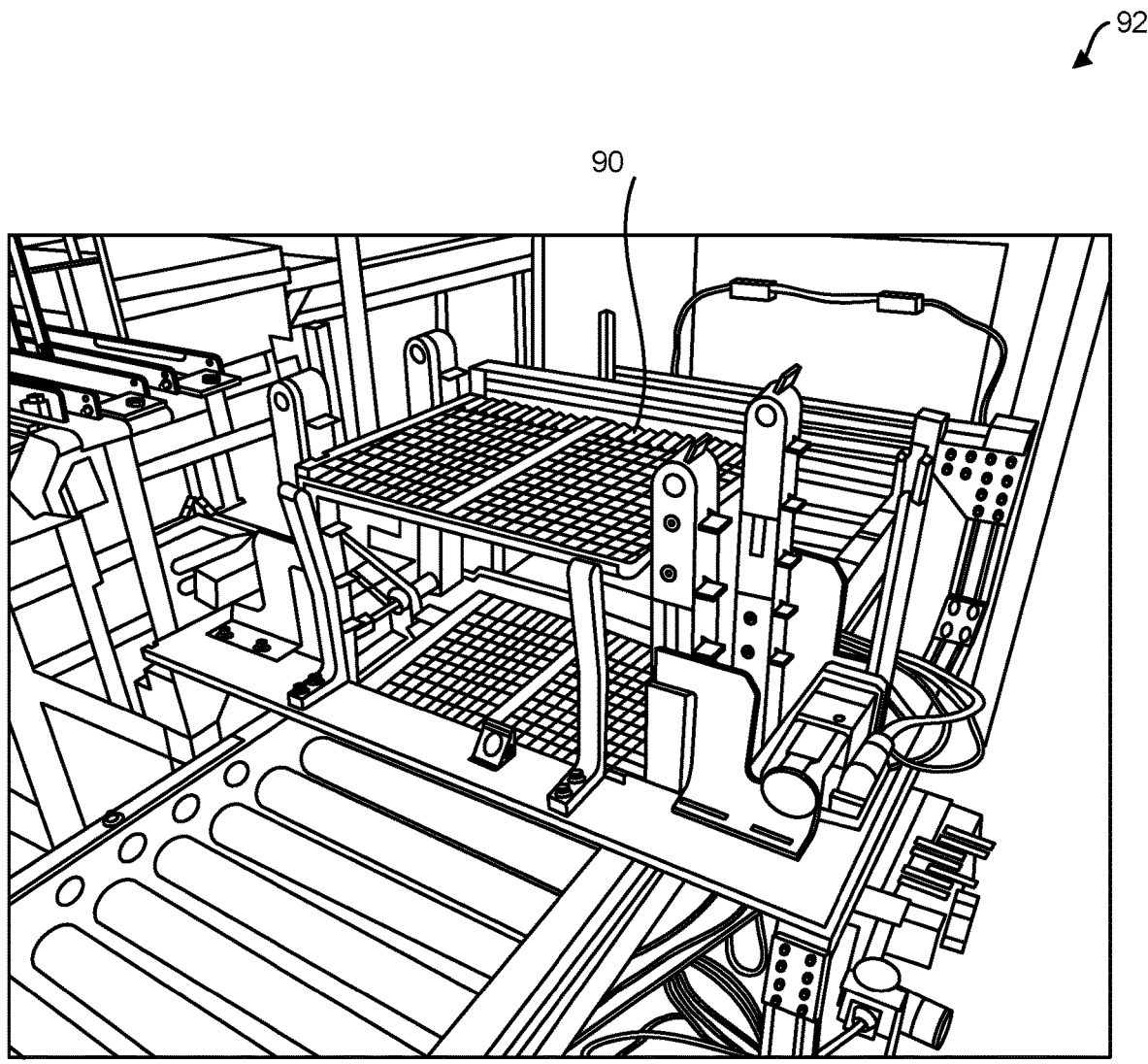
FIG. 10B is an image of the template and lowerator station.

In one or more embodiments, a backlit template 94 may be used to improve the throughput of the processes described herein by improving seed counting accuracy and subsequently removing any required manual oversight. As shown in FIGS. 10A and 10B, the template 94 is placed onto a media-filled planting tray 70, 72 at the template placing station 92 installed on the automation line. The tray 70, 72 containing the template 90 is moved by conveyor 76 to the seed planting station 82. The template 94 and tray 70, 72 pass through the seed planting station 82 where the seeder 86 (e.g., modified cylinder seeder) places a specified number of seeds into the array of pockets or channels (e.g., wells) in the planting template 94. The seeds do not generally need to pass through the template 94 to rest on the planting media, but instead rest on a light diffuser within the backlit planting template 94.

The template 94 and tray 70, 72 exit the seed planting station 82 and stop at a specified location on the conveyor 76. The tray 70, 72 is then moved by a conveyor-mounted power system to establish alignment and electrical connectivity with power connectors on the side of the template. The power system verifies that the electrical connection was successful and supplies power to the onboard light source 122 (e.g., light emitting diodes (LEDs)) to illuminate the light diffuser 98. An overhead smart camera, such as imaging system 160 described below, captures and processes an image, and subsequently delivers seed counts to the control system of the automated line.

A robot can then move into position above the planting template 94 and use a gripper or similar apparatus to engage the edges of the template 94. In this way, the robot maintains a hold on the template 94 and a device moves the template top (e.g., a gripper-mounted air cylinder), which then releases the counted seeds onto the planting media contained in the tray 94. In some instances, the robot may release, re-energize, and release again the air cylinder (or similar device) to ensure that all seeds have been dropped. The robot can then remove the planting template 94 from the tray 70, 72 and place it back into the template dropping mechanism for reuse.

Figure 17:
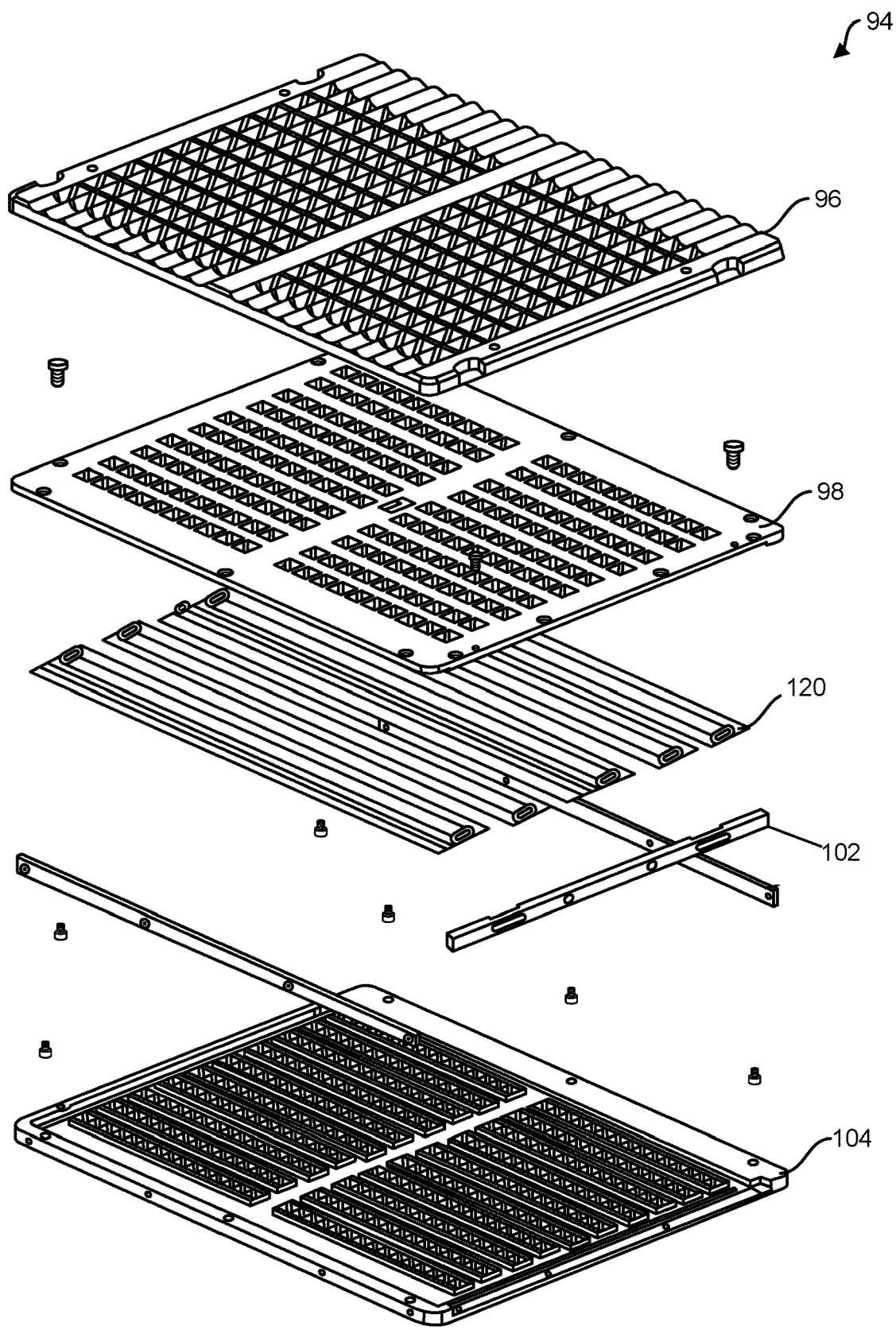
FIG. 17 is an exploded view of a backlit template.
Figure 18:
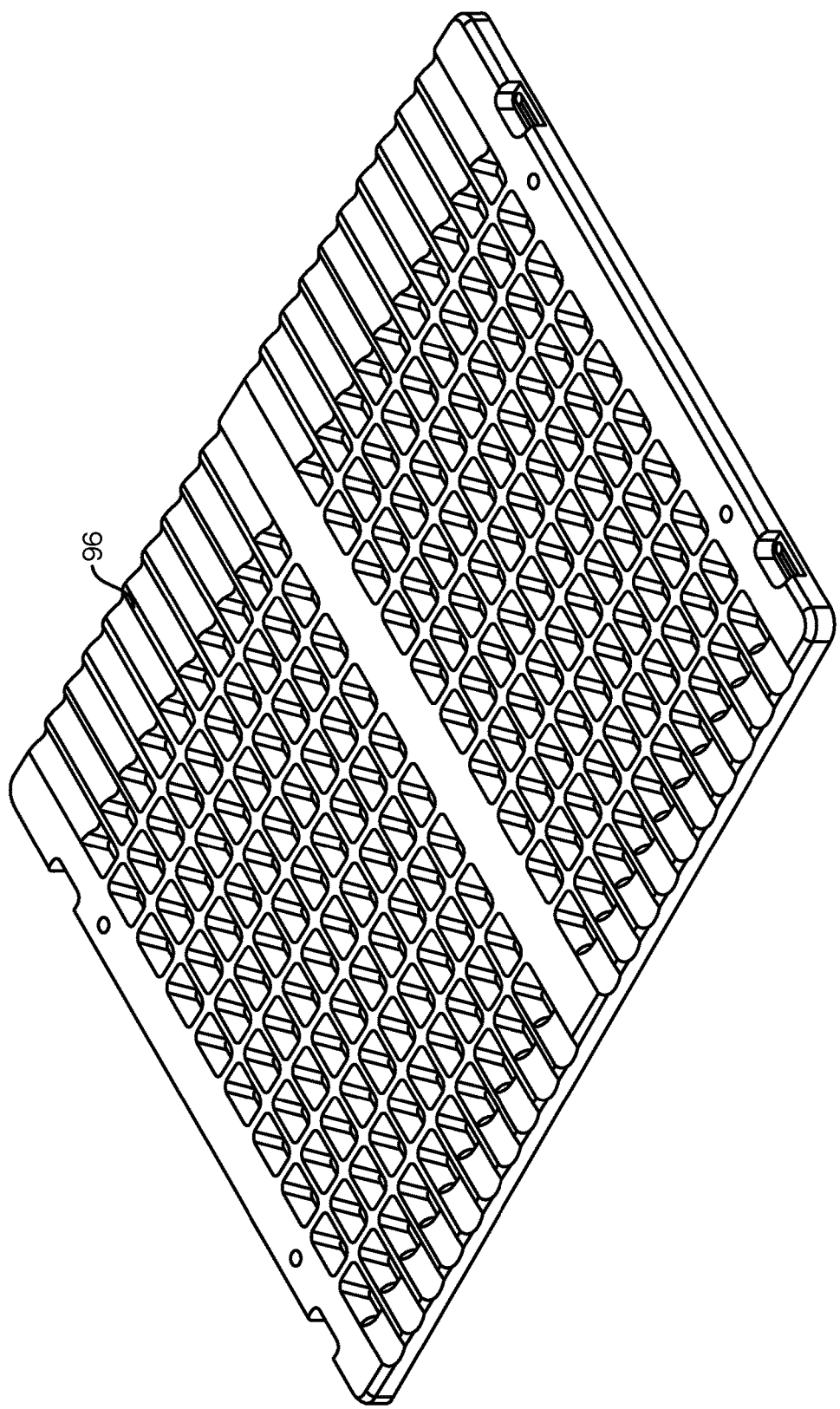
FIG. 18 is a perspective view of a template top of the backlit template.
Figure 19:
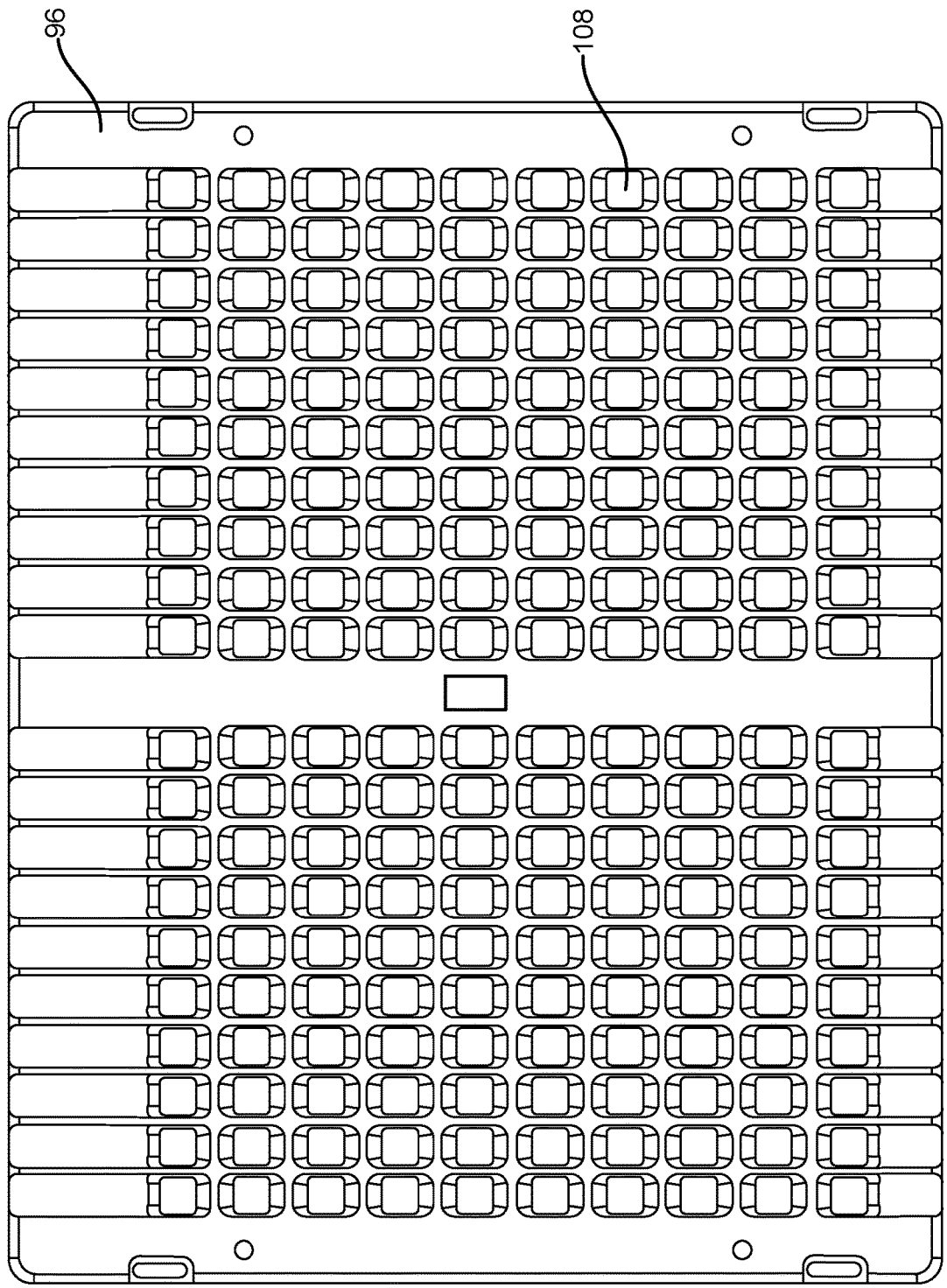
FIG. 19 is a top view of the template top.

In general, and referring to FIG. 17, the backlit template 94 comprises a template top 96, a light guide 98, printed circuit boards 120, a power interface 102, and a template bottom 104. Referring to FIGS. 18 and 19, the template top 96 contains channels (e.g., wells) 108 that receive seeds from the cylinder seeder 86 and subsequently aligns them into the correct spacing on top of the light guide 98. The template top 96 contains a specified number of planting channels 108. In various embodiments, the planting channels 108 may be separated into more than one zone for disparate samples. The template top 96 can also serve as a movable escapement of the planting template 94. The template top 96 is generally constructed of a clear material, for example, a clear, vapor polished polycarbonate, to enable sufficient lighting of the template 94 for imaging purposes.

Figure 29B:
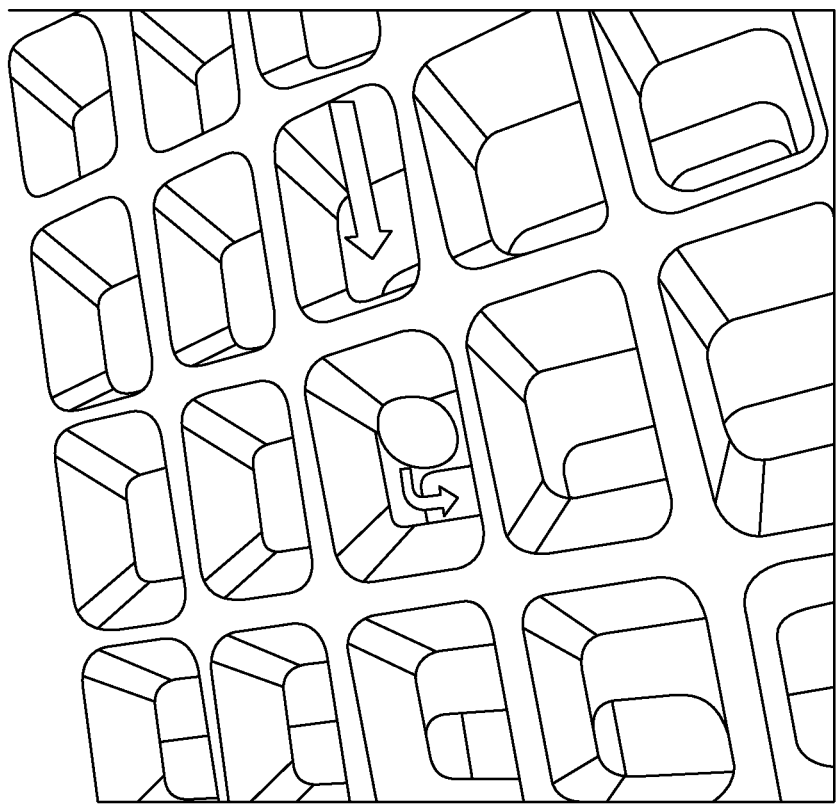
FIG. 29B is an image of an open template for escapement.
Figure 29A:
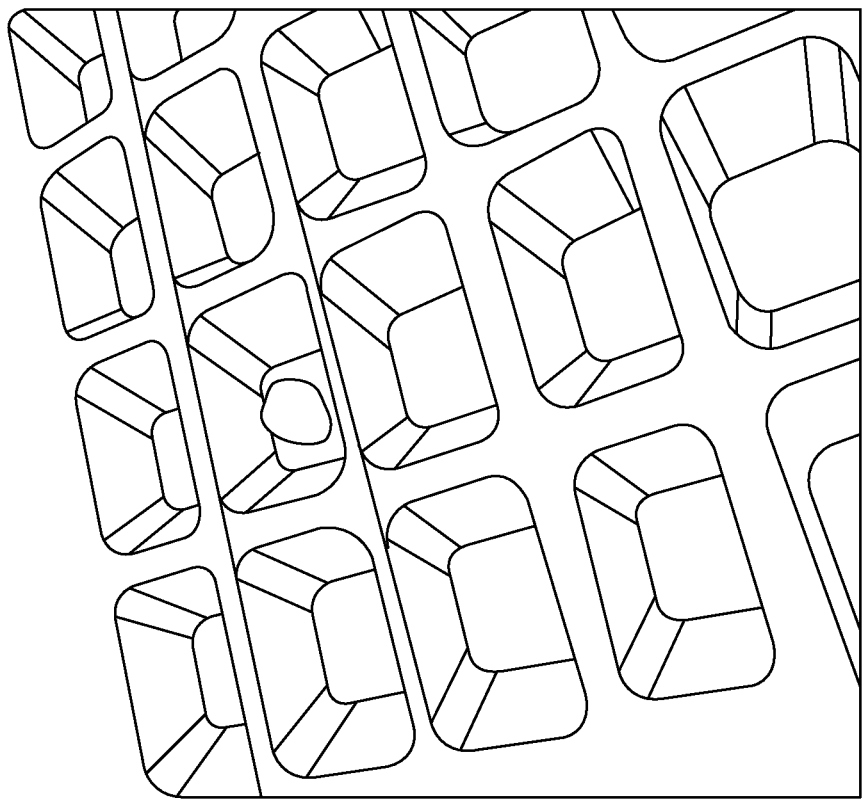
FIG. 29A is an image of a closed template for imaging.
Figure 30:
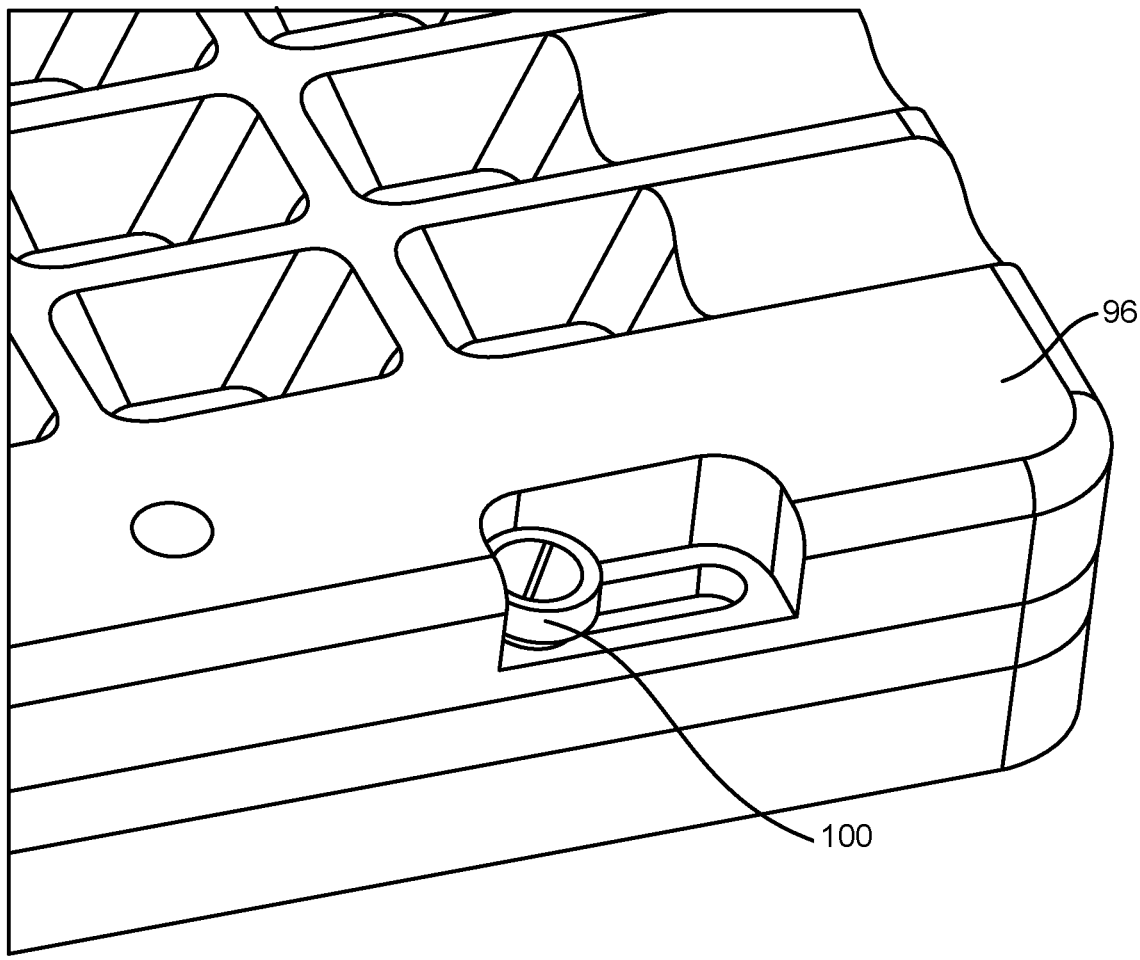
FIG. 30 is a perspective view of a portion of the template top depicting the cam roller.

The template top 96 can serve as the movable escapement by moving directions (e.g., side-to-side or back and forth) and pushing the seed into the hole exposed by the moving top. The seed then falls through the exposed hole and onto the media within the planting tray 70, 72 (see FIGS. 29A and 29B, depicting a seed falling through the exposed hole). The escapement can be guided by a cam roller 100 installed in a machined slot in the template top 96 (see FIG. 30).

Figure 20:
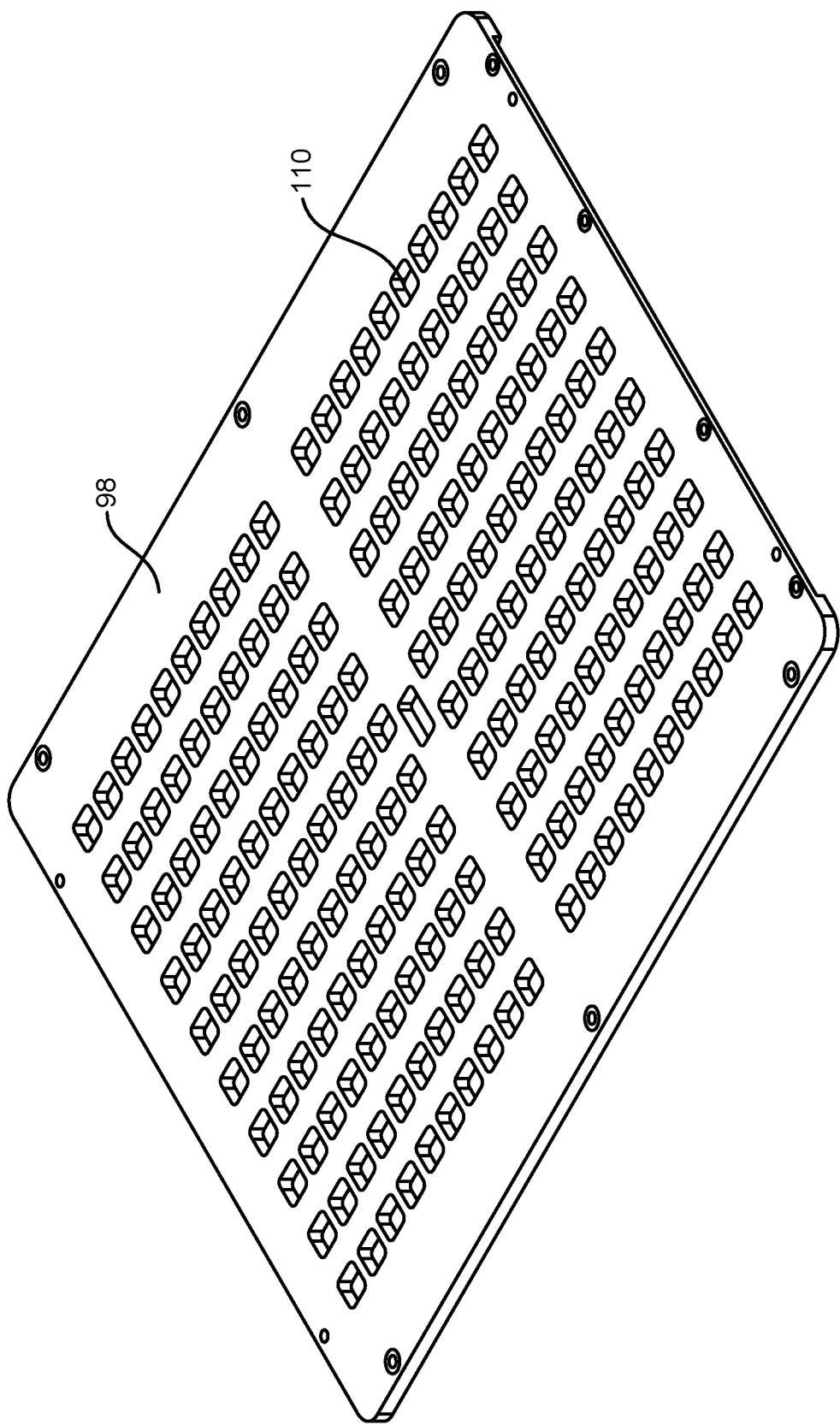
FIG. 20 is a perspective view of a light guide of the backlit template.

Referring to FIG. 20, the light guide 98 is located directly below the template top 96. The light guide 98 covers the template-mounted LEDs and diffuses their light to provide a uniformly lit imaging area. The light guide 98 is constructed of semi-translucent material, for example, a semi-translucent polymer, e.g., a semi-translucent, white ultra-high molecular weight polyethylene. The light guide 98 contains a specified number of channels 110 (e.g., wells) that are offset from the channels 108 of the template top 96 before the template top 96 is actuated. The channels 108, 110 in the template top 96 and the light guide 98 generally align as the template top 96 is actuated, allowing the seeds to pass through. The light guide 98 can also contain a pocket that houses a compression spring to return the template top 96 into the closed position after it is released by the robot (not shown).

Figure 21:
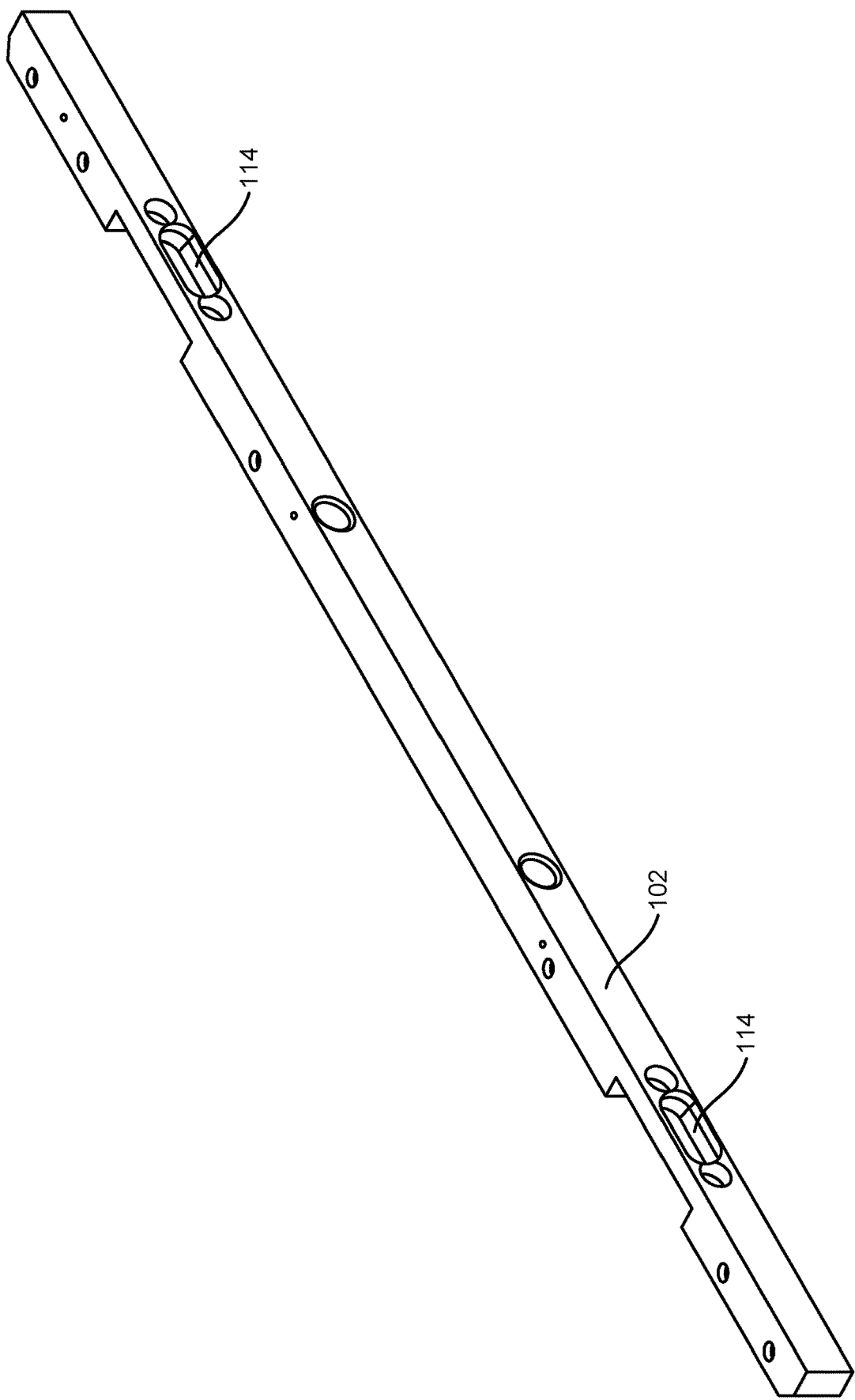
FIG. 21 is a perspective view of an alignment and power mount of the backlit template.

Referring to FIG. 21, the alignment and power mount 102 can be installed in the side of the planting template 94. The mount 102 can be made of a plastic, e.g., a PEEK (polyether ether ketone) plastic, to prevent binding with the mating pins of the alignment plate and to prevent unwanted conductance of electricity. The mount can contain at least one pocket 114, for example, two pockets, that each house a target connector that receives power from the conveyor-mounted power system. The mount can also contain at least one alignment hole, for example, two alignment holes, that receive an alignment pin as the power and actuation system engages.

Figure 22:
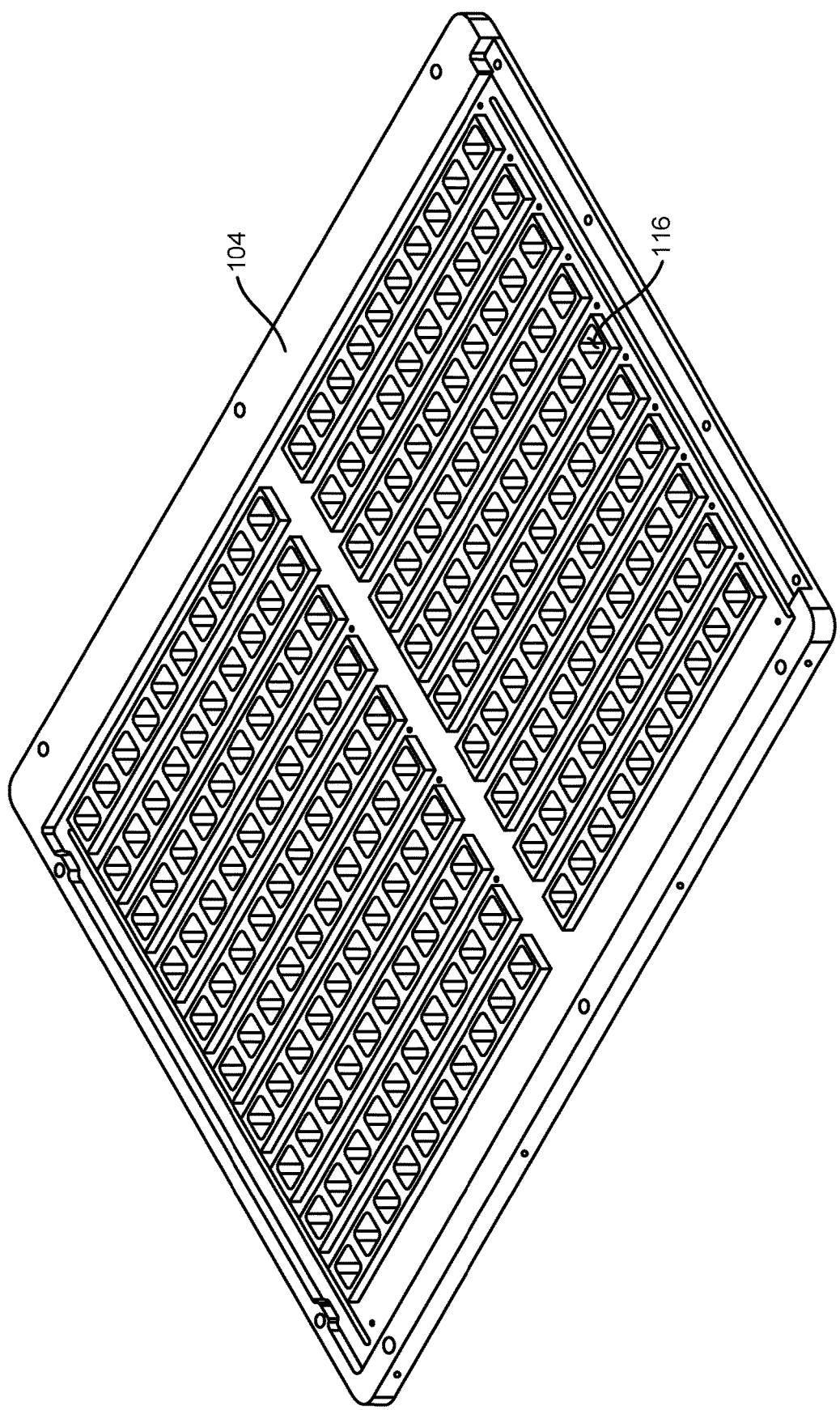
FIG. 22 is a perspective view of a template bottom of the backlit template.

In general, the template bottom 104 (FIG. 22) is rigidly attached (e.g., bolted) to the light guide 96. The template bottom 104 has channels 116 (e.g., openings) that align with the channels 110 of the light guide 96. The template bottom 104 can also contain a pocket that house the printed circuit boards and light source (e.g., LEDs) that illuminate the planting area 82. The underside of the template bottom 104 can be shaped to fit within the tapered sides of the planting trays 70, 72. In some embodiments, the template bottom 104 is constructed of a semi-translucent material, for example, a semi-translucent polymer, e.g., a semi-translucent, white ultra-high molecular weight polyethylene.

Figure 23:
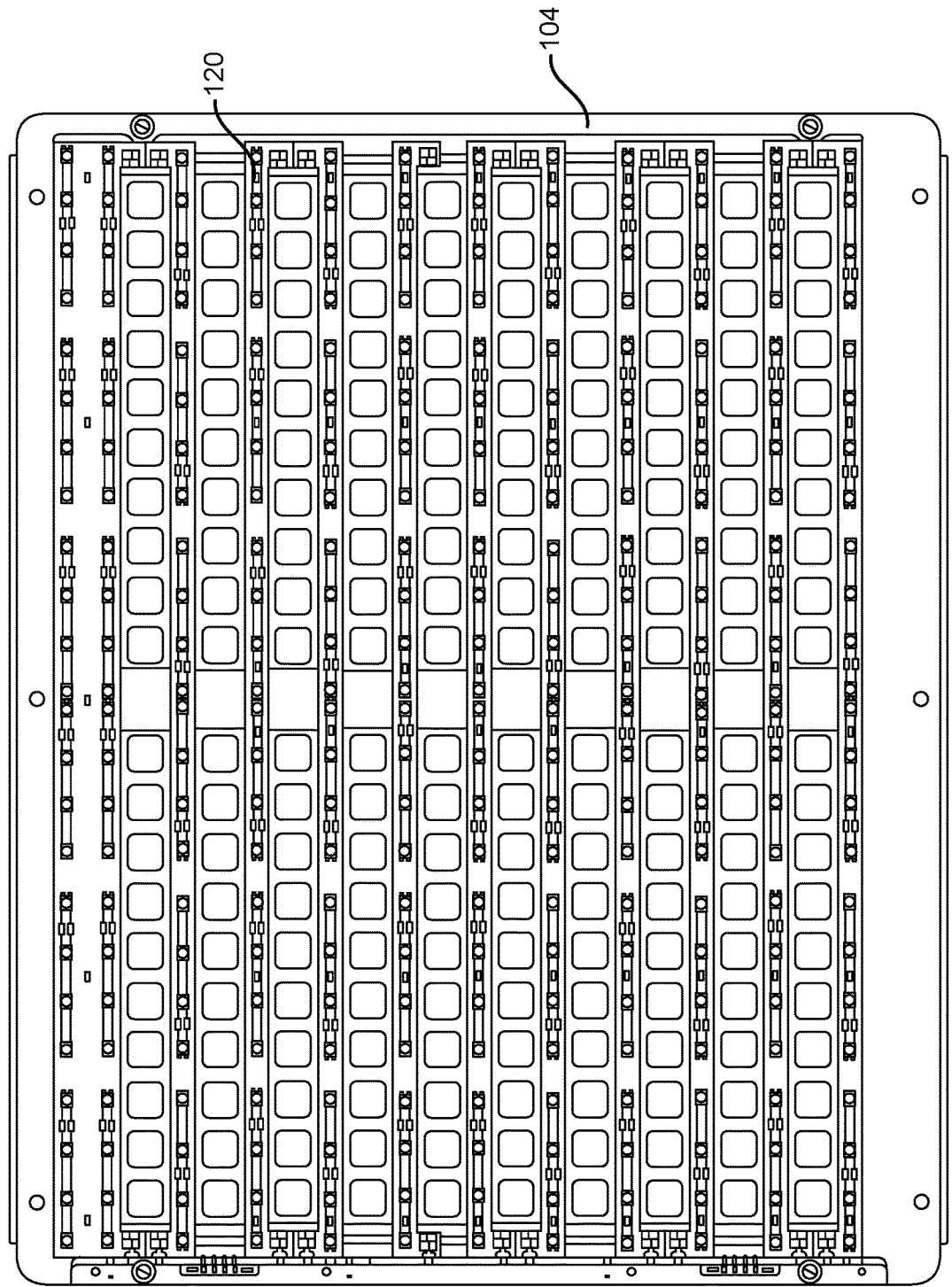
FIG. 23 is a top view of the template bottom depicting the printed circuit boards.
Figure 24A:
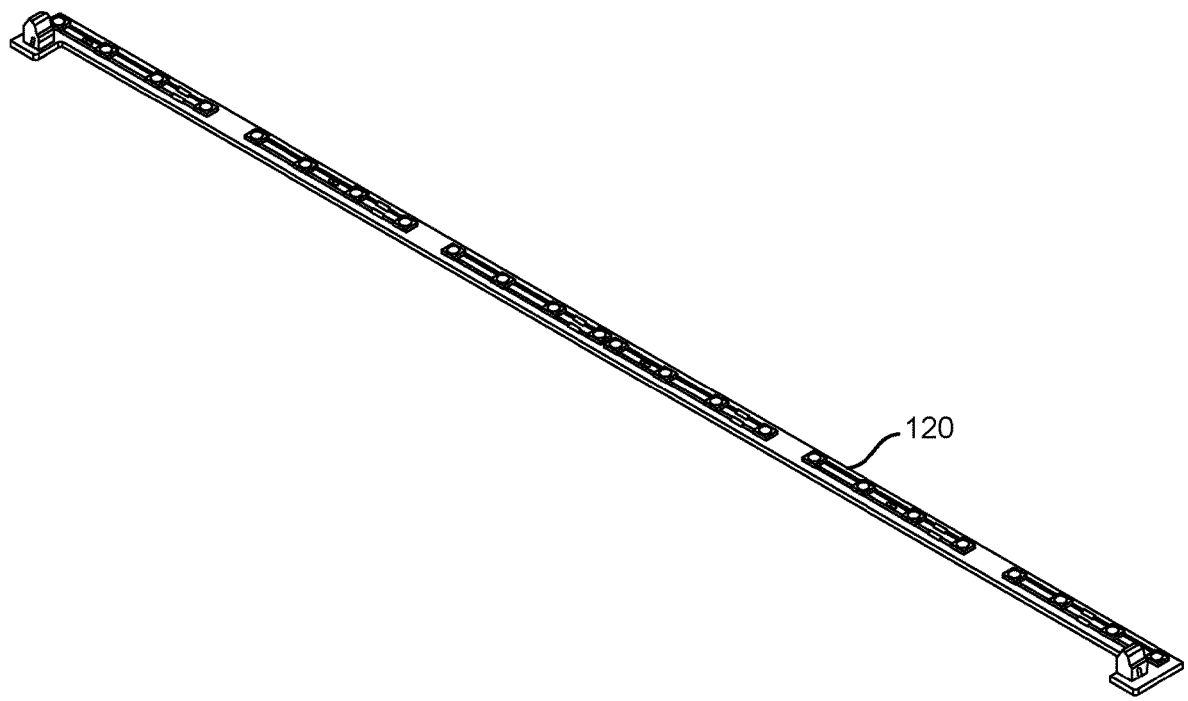
FIG. 24A is a perspective view of a printed circuit board having one row of LEDs.
Figure 24B:
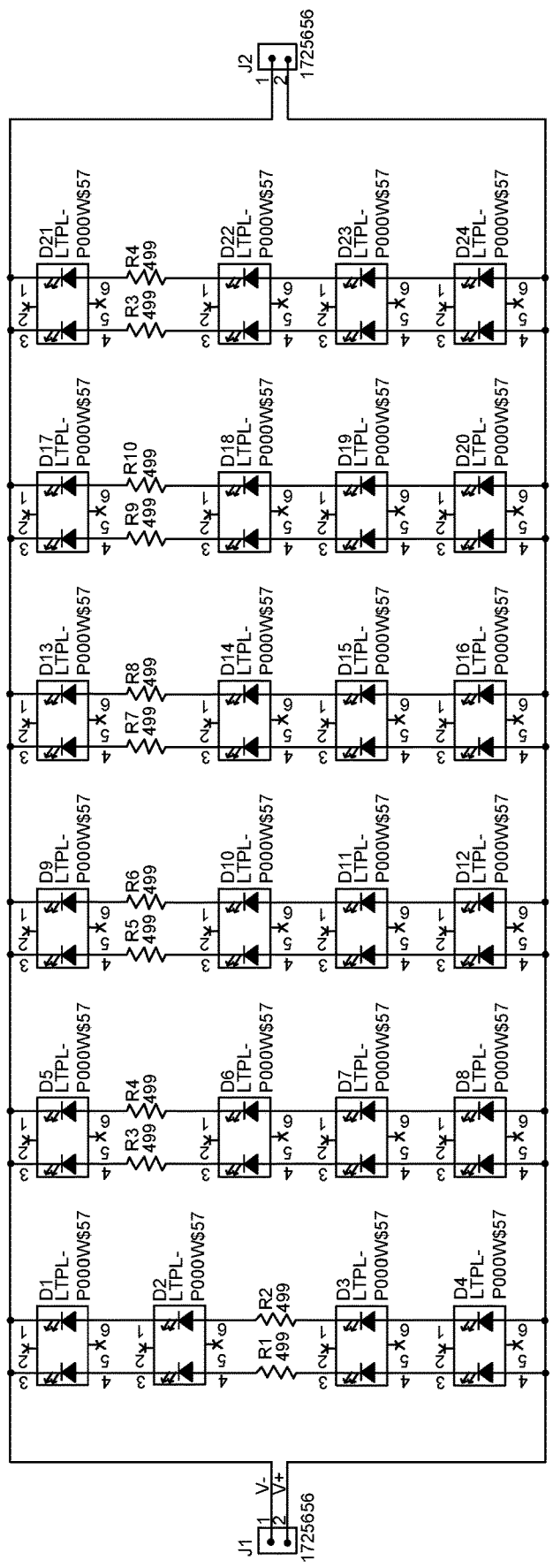
FIG. 24B is a diagram of a printed circuit board having one row of LEDs.
Figure 25:
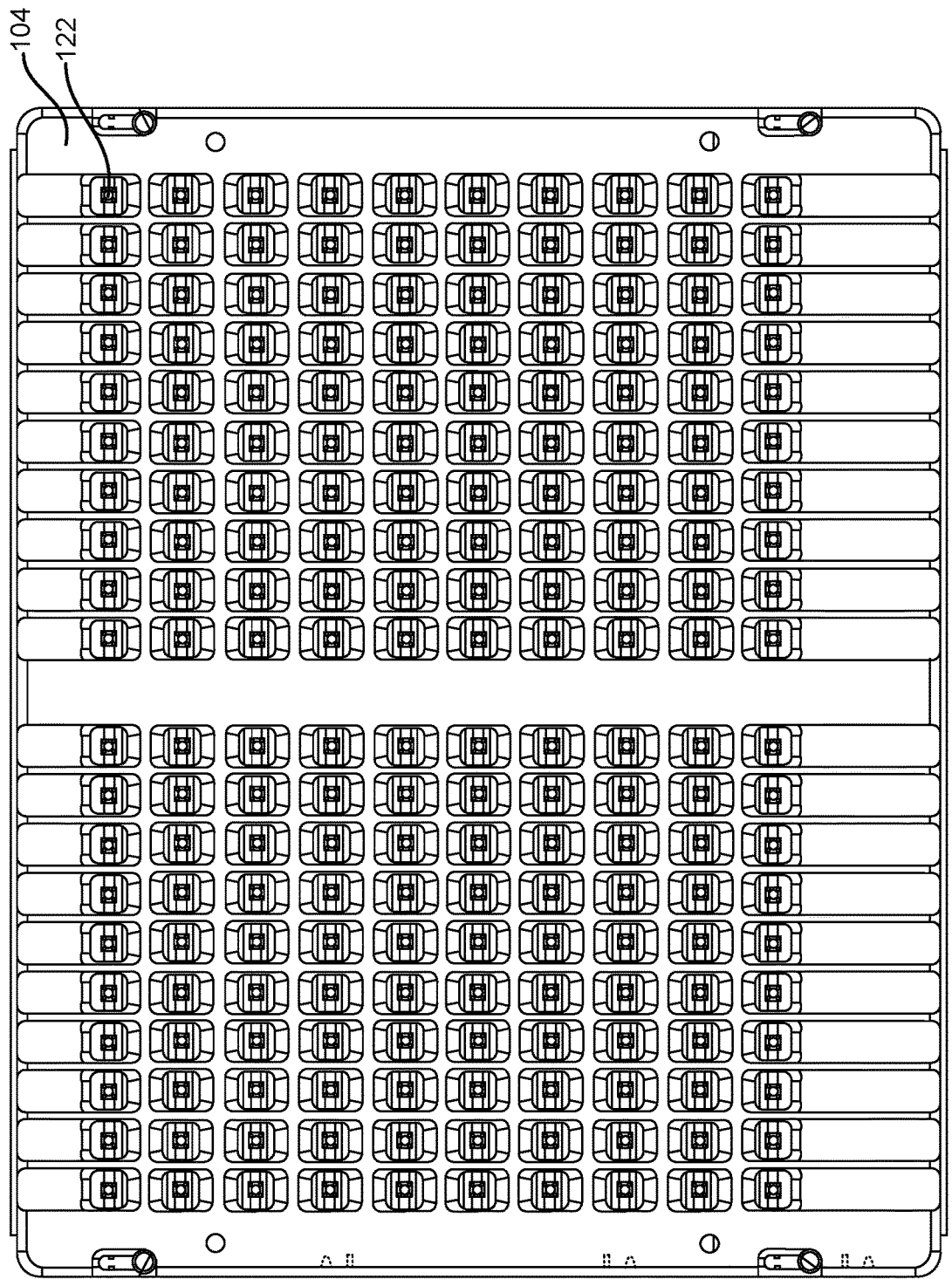
FIG. 25 is a top view of the template depicting the alignment of LEDs and planting channels (light guide hidden).
Figure 26:
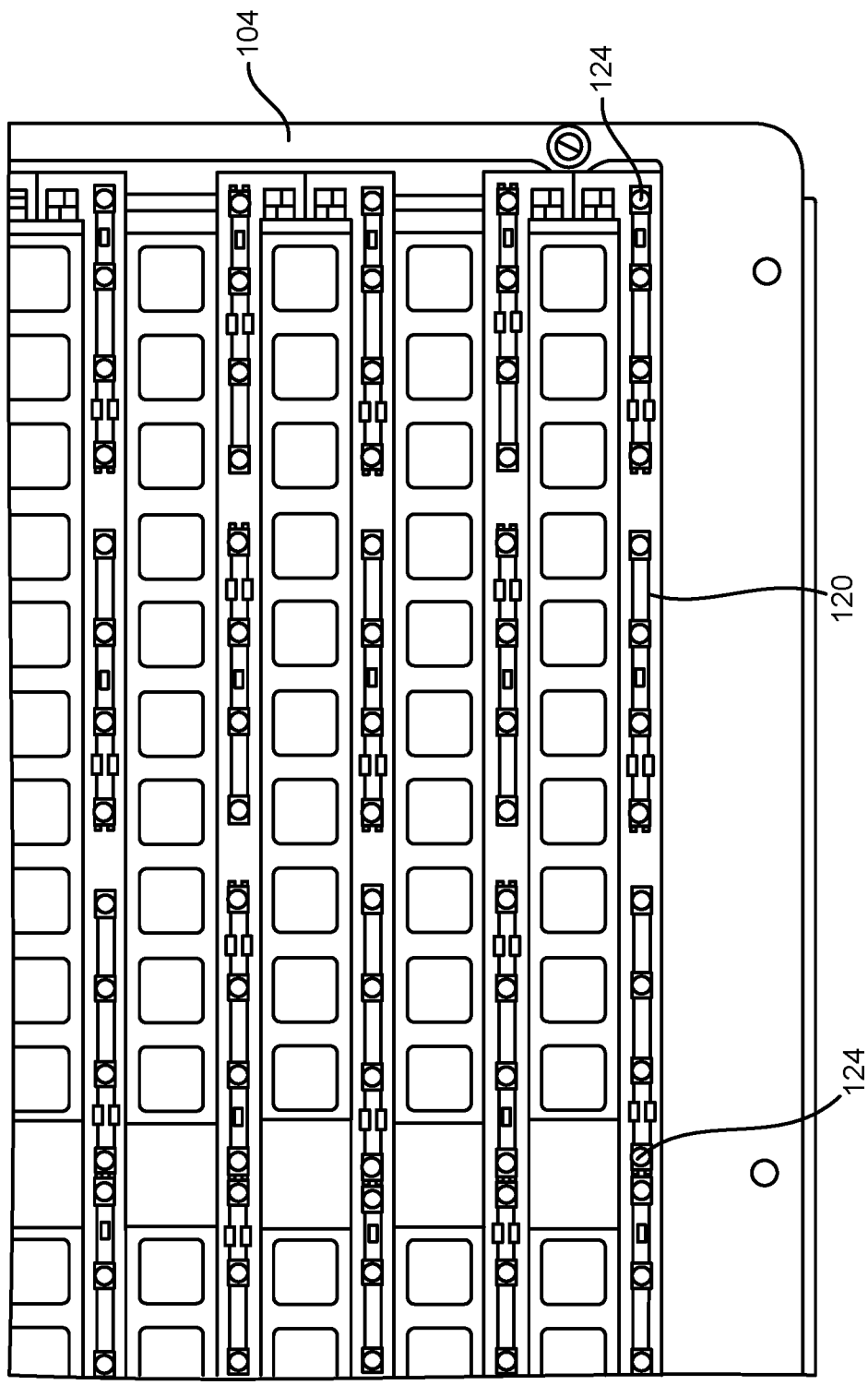
FIG. 26 is a top view of a portion of the template bottom depicting perimeter LEDs.
Figure 27A:
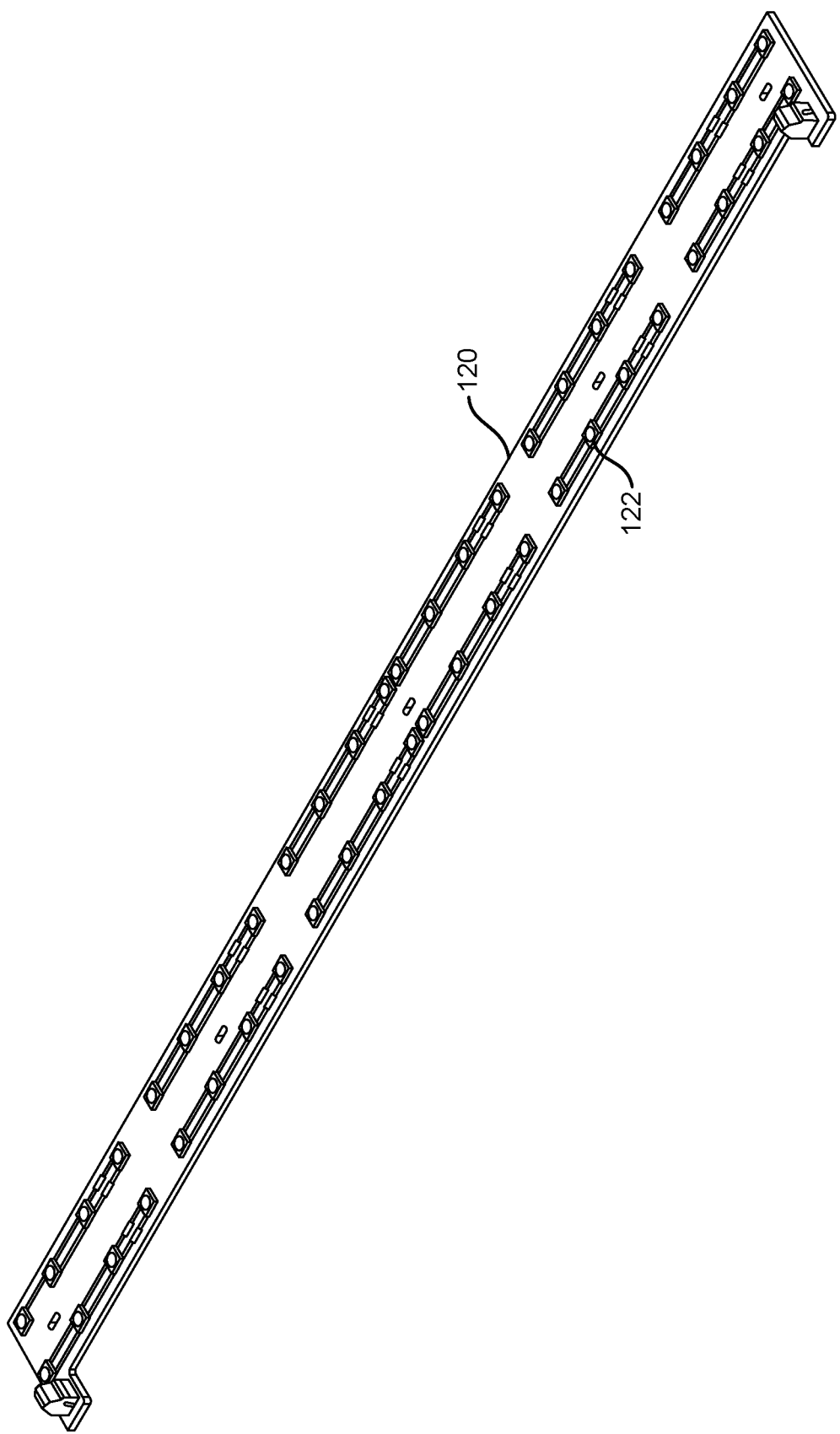
FIG. 27A is a perspective view of a printed circuit board having two rows of LEDs.
Figure 27B:
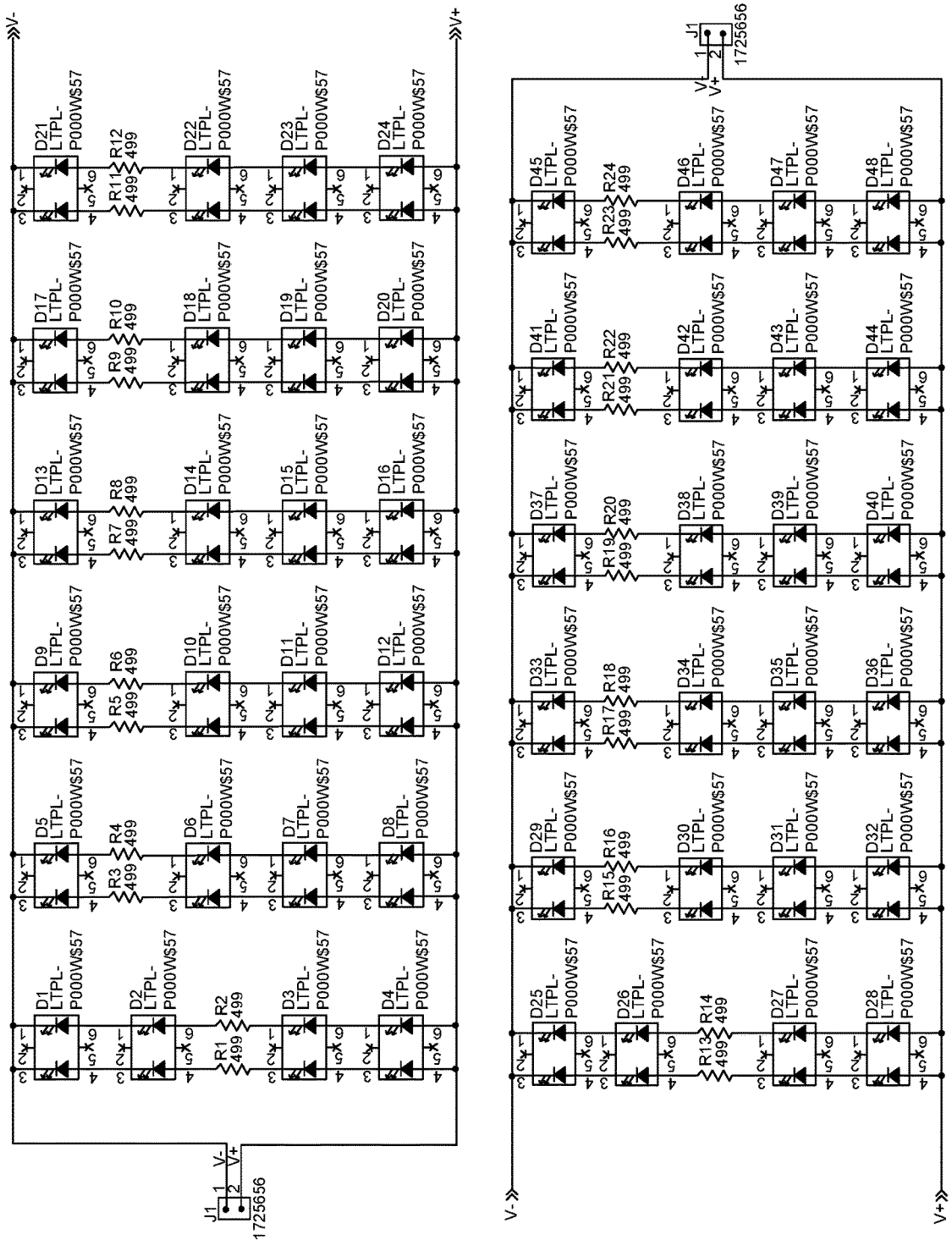
FIG. 27B is a diagram of a printed circuit board of two rows of LEDs.
Figure 28A:
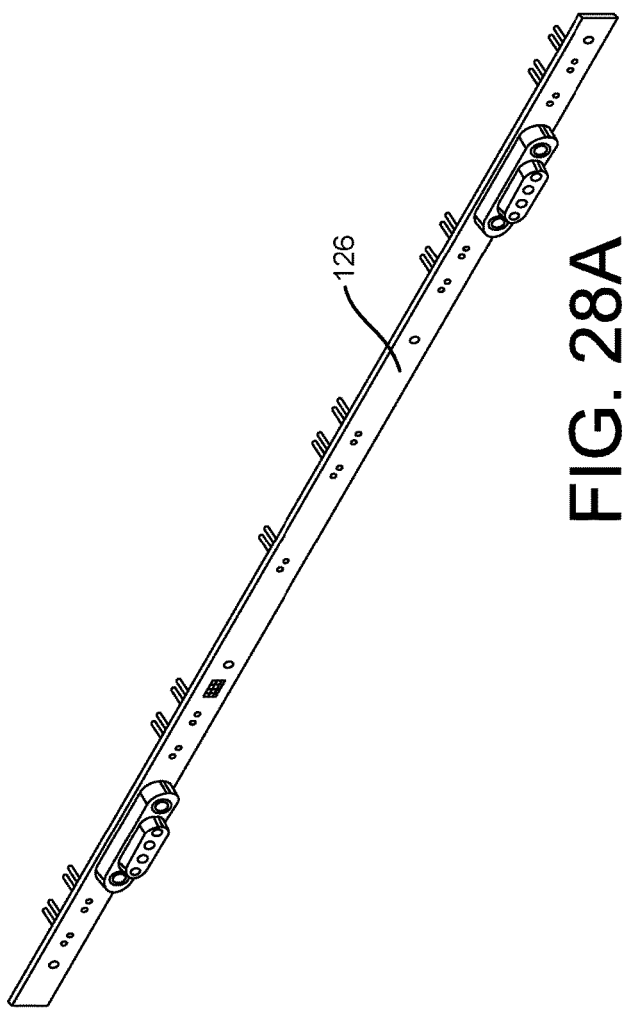
FIG. 28A is a perspective view of a power bus.
Figure 28B:
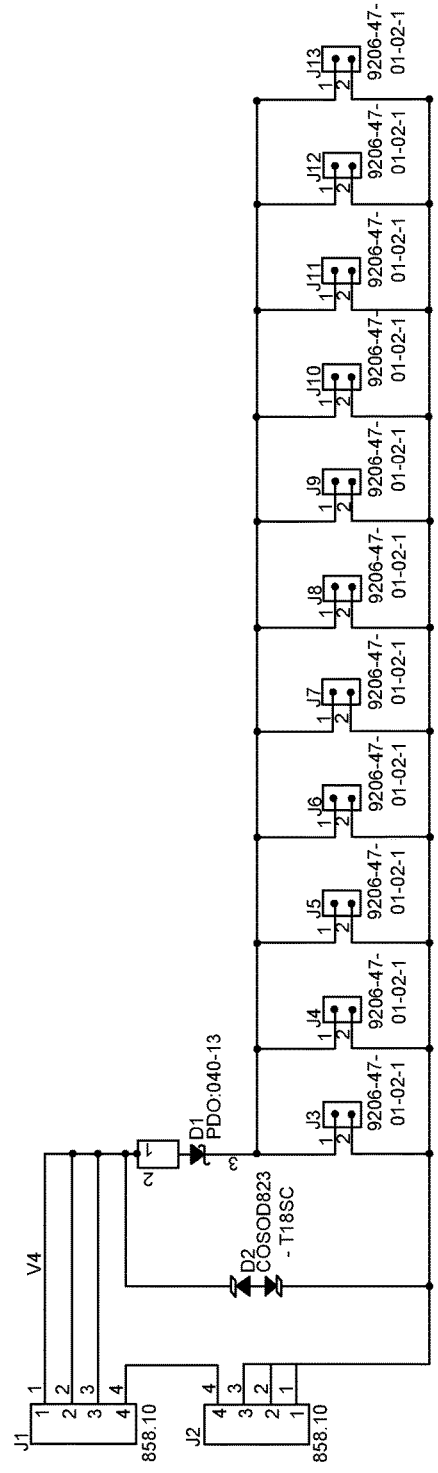
FIG. 28B is a diagram of a power bus.

Referring to FIG. 23, the template 94 contains at least one printed circuit board (PCB) 120. For example, the template can contain at least one, at least two, at least three, at least four, at least five, at least six, at least seven, at least eight, at least nine, at least ten, at least 11, at least 12, at least 13, at least 14, or at least 15 PCBs. In general, the light source 122 (e.g., LED) spacing can match the channel spacing of the template light guide 98 and template bottom 104. FIGS. 24A and 24B depict a single row of LED-containing PCBs 120. In some embodiments, one LED 122 is positioned under each of the planting channels to provide a direct backlight (see FIG. 25). Additional LEDs can be placed at the end of each row of channels to provide a uniform perimeter lighting 124 (see FIG. 26). The template 94 can contain an additional PCB 120 which contains an additional row of LEDs 122 to provide perimeter lighting (see FIGS. 27A and 27B). The template can also contain an additional PCB 120 known as the Power Bus 126 to transfer power from the conveyor-mounted power system to the LED-containing PCBs 120 (see FIGS. 28A and 28B).

Figure 31:
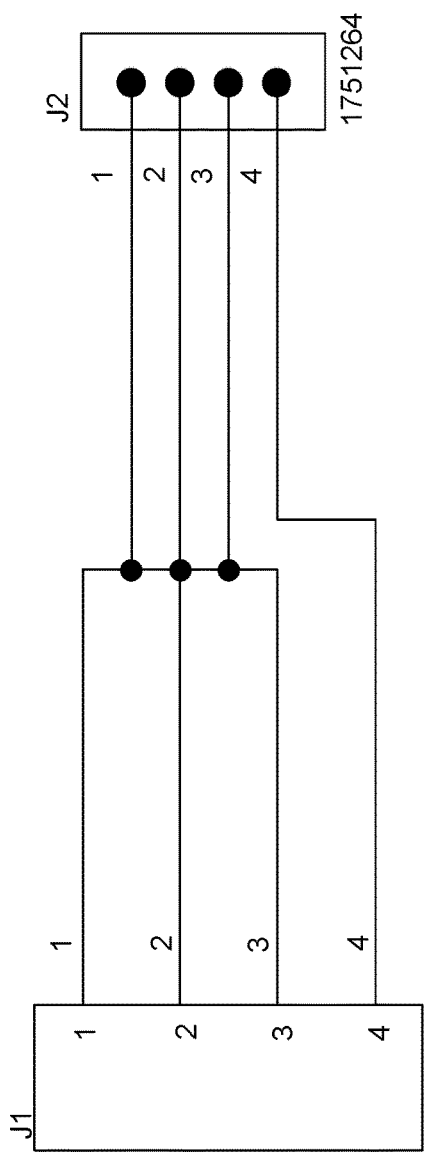
FIG. 31 is a schematic of the template power connector printed circuit board.
Figure 32:
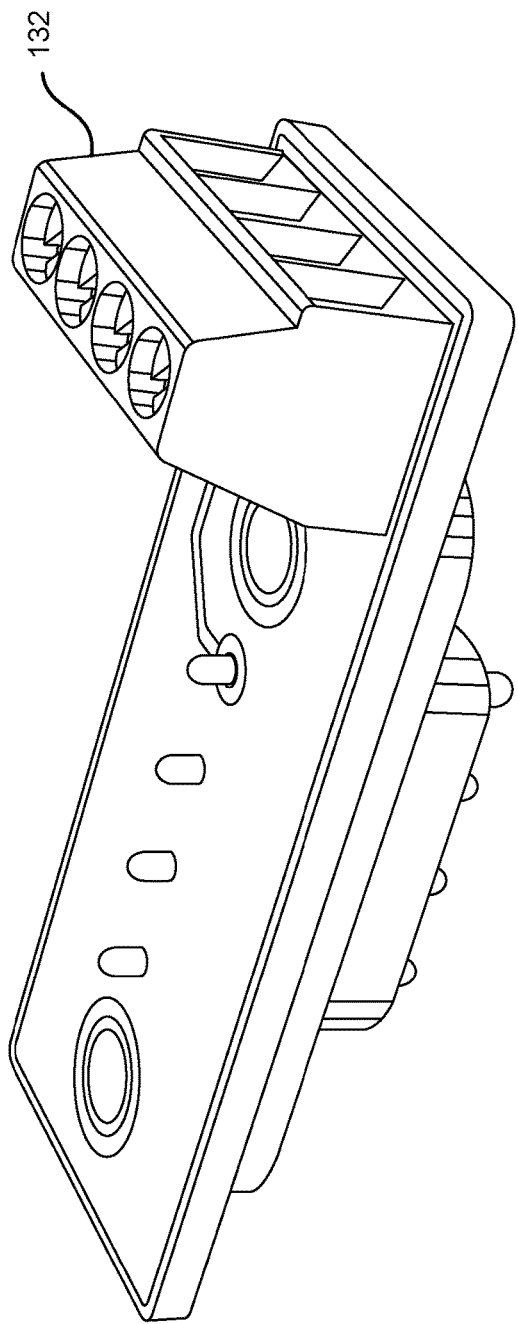
FIG. 32 is a perspective view of the template power connector.
Figure 33:
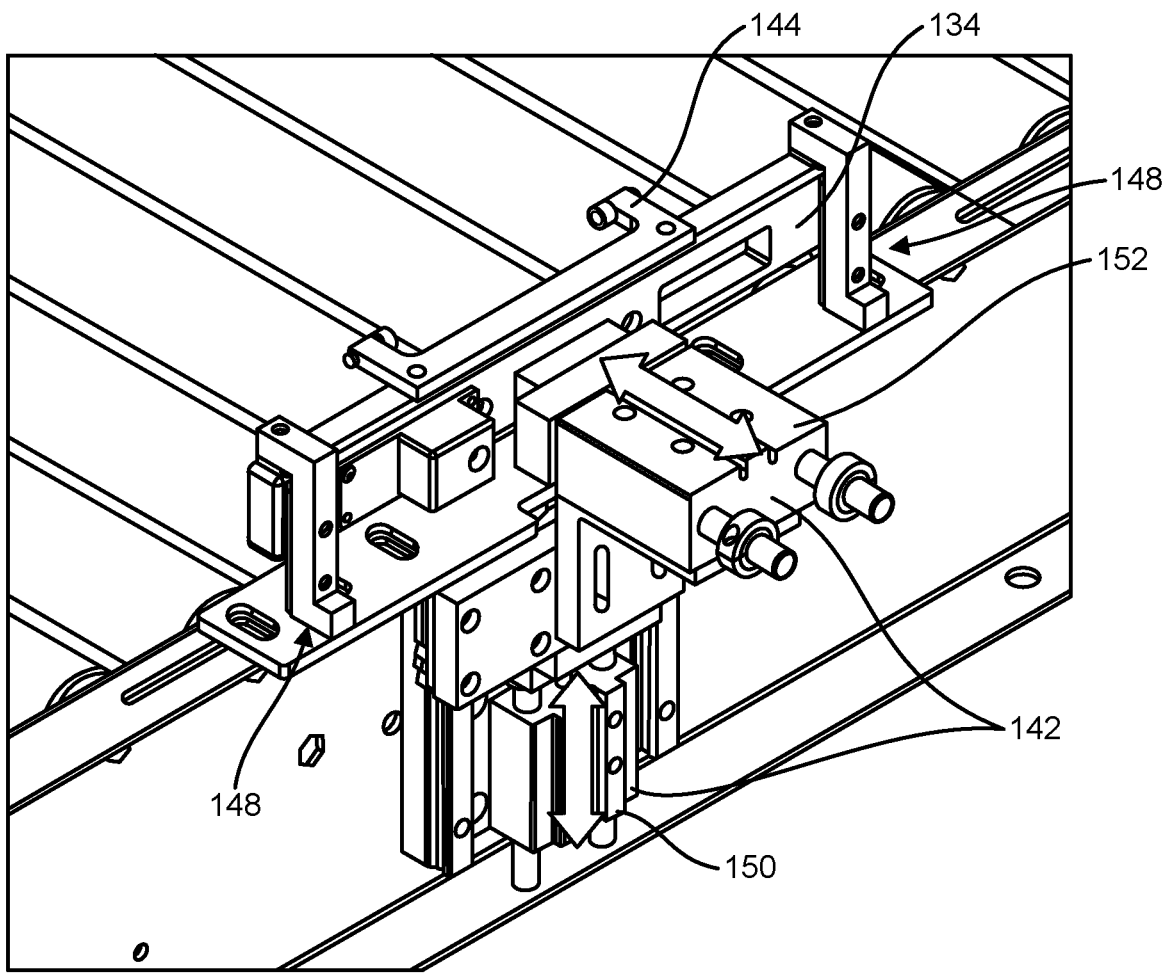
FIG. 33 is a perspective view of a portion of the conveyor depicting the actuation of the power system.
Figure 34:
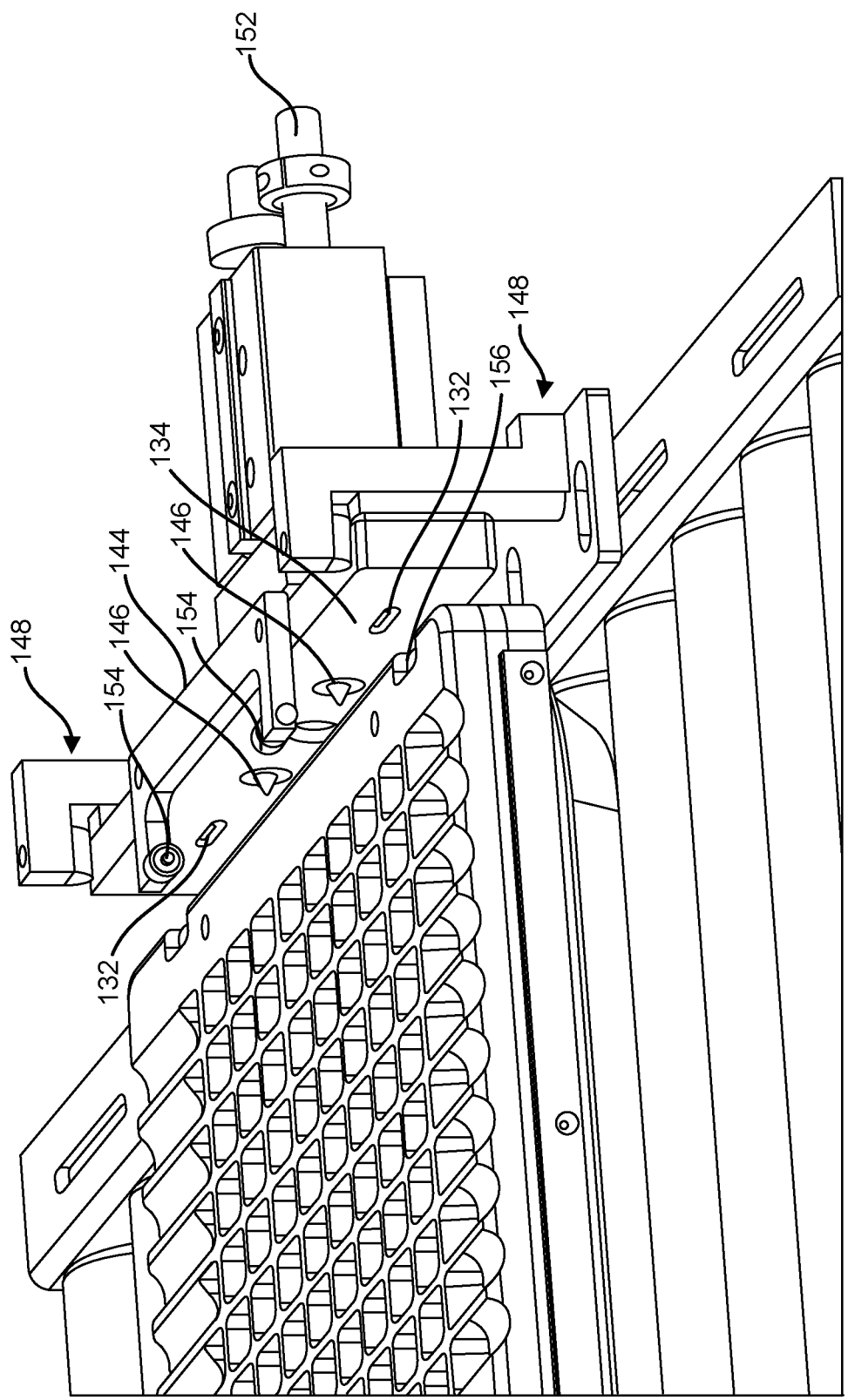
FIG. 34 is an image of the template in the starting position.
Figure 35:
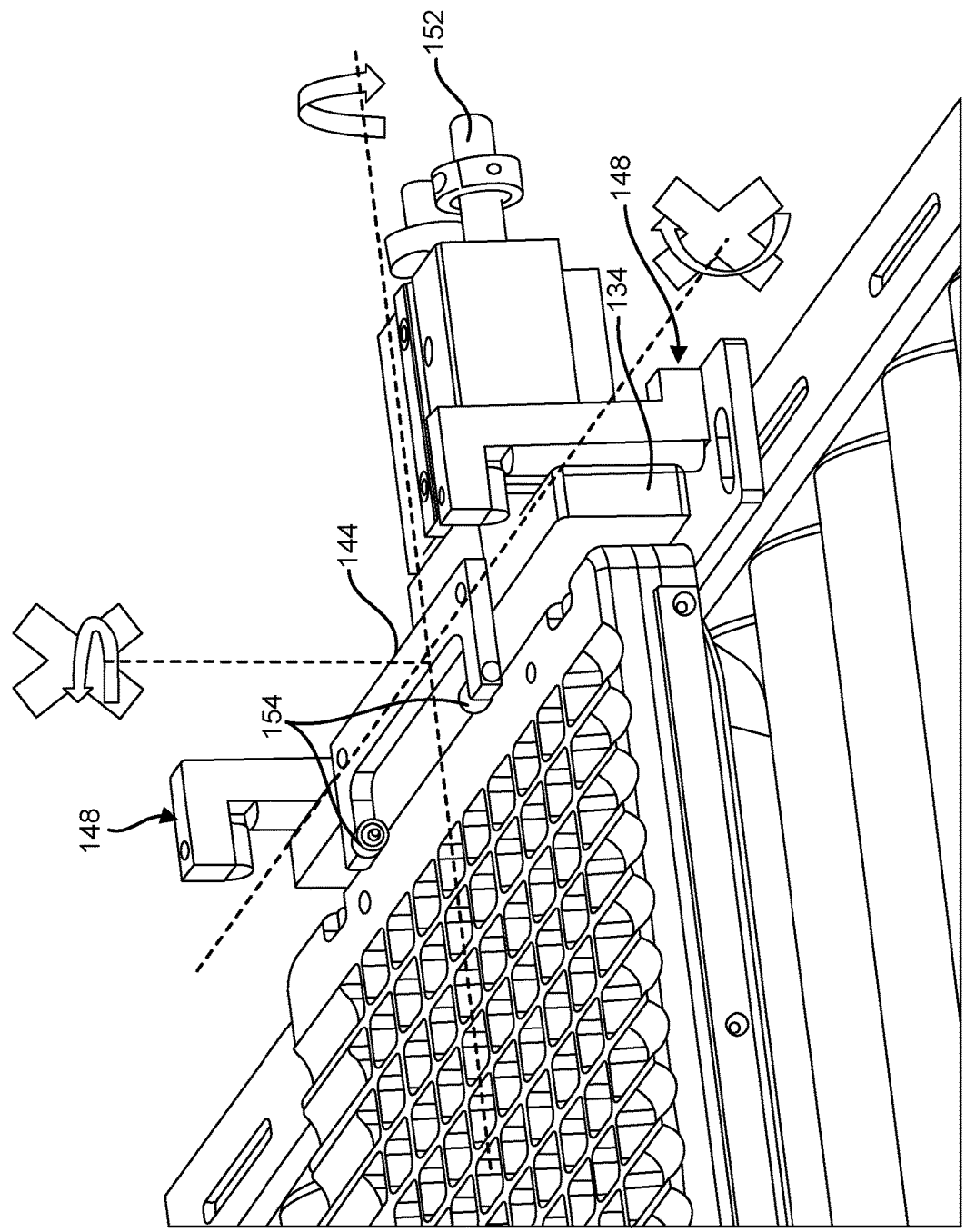
FIG. 35 is an image of the template in the intermediate position.

The power system also moves the tray to establish the correct alignment and electrical connectivity with power connectors 132 on the side of the template 94 (see FIGS. 31 and 32). Referring to FIGS. 33 to 36, the power system comprises, in general, at least one adjustable air slide 142 (e.g., two air slides), an alignment plate 144 containing at least one power connector 132 (e.g., two power connectors) and at least one alignment pin 146 (e.g., two alignment pins), and travel-stops 148. The alignment pins 146 and power connectors 132 interface with alignment holes and power connectors on the planting template 94.

Figure 36:
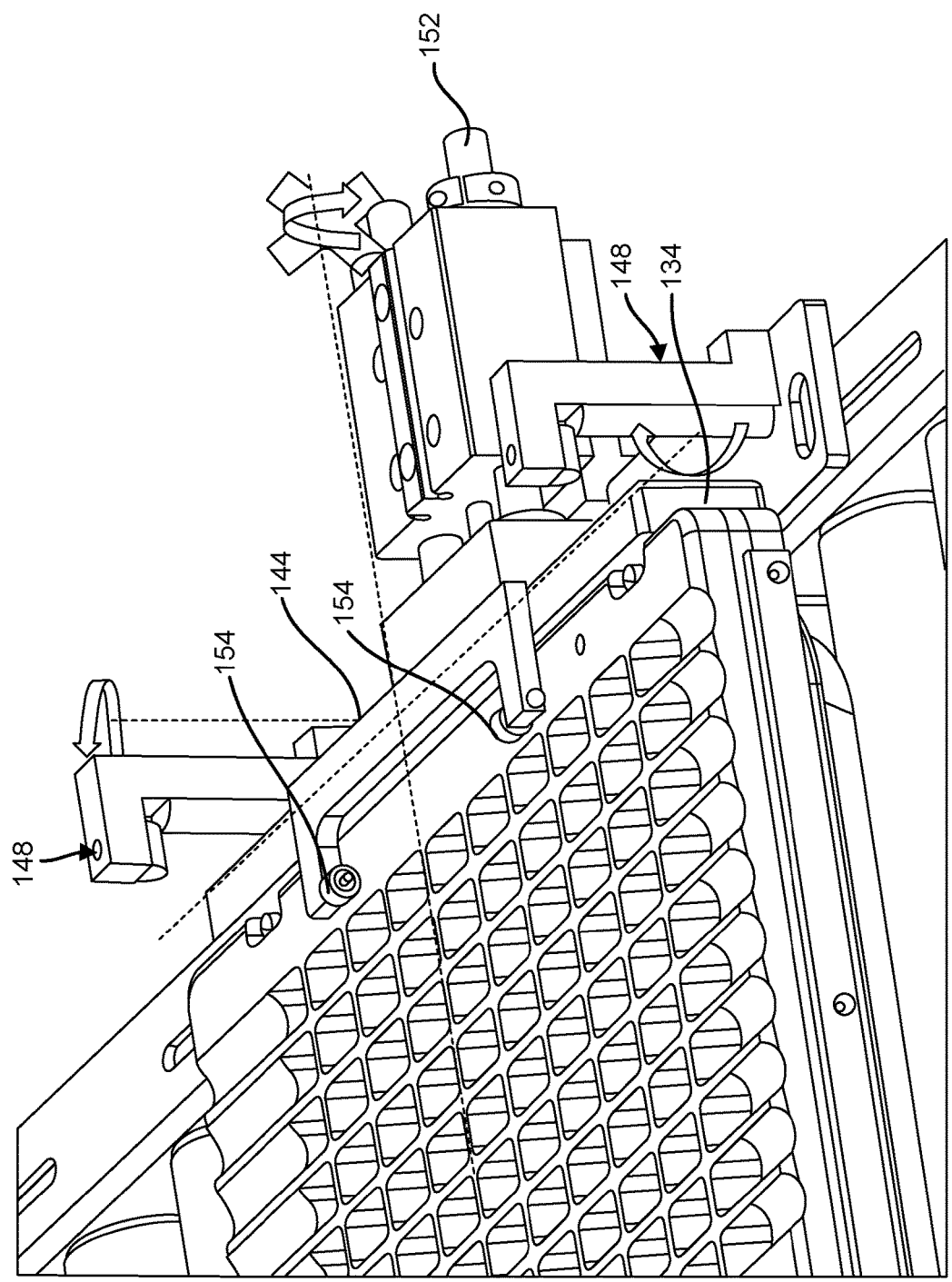
FIG. 36 is an image of the template in the powered position.

The backlit template power system has three primary positions: starting (FIG. 34), intermediate (FIG. 35), and powered (FIG. 36). A vertical lift cylinder 150 can be extended and the horizontal cylinder 152 can be retracted to position the alignment plate 144 against top and back travel-stops in the starting position. In this way, the power bar 134 is realigned for the incoming template 94. The vertical lift cylinder 150 is retracted to a known position, depending on the tray style, to achieve the intermediate position. A spherical bearing 156 attached to the alignment plate 144 allows the alignment plate 144 to rotate and align to the top surface of the template 94 as the vertical lift cylinder 150 is retracted. The alignment plate 144 remains against the back travel-stop 148 to ensure that rotation only occurs in the desired axis. The horizontal cylinder 152 extends and moves the alignment plate 144 away from the back travel-stops 148, and the alignment pins 146 engage the mating holes in the template 94. Guide wheels 154 on top of the alignment plate 144 roll along the top surface of the template 94. The spherical bearing 156 allows minimal movement in the remaining two directions enabled after the alignment plate 144 is moved forward in order to ensure positive engagement of the alignment plate 144 and template 94.

Figure 37:
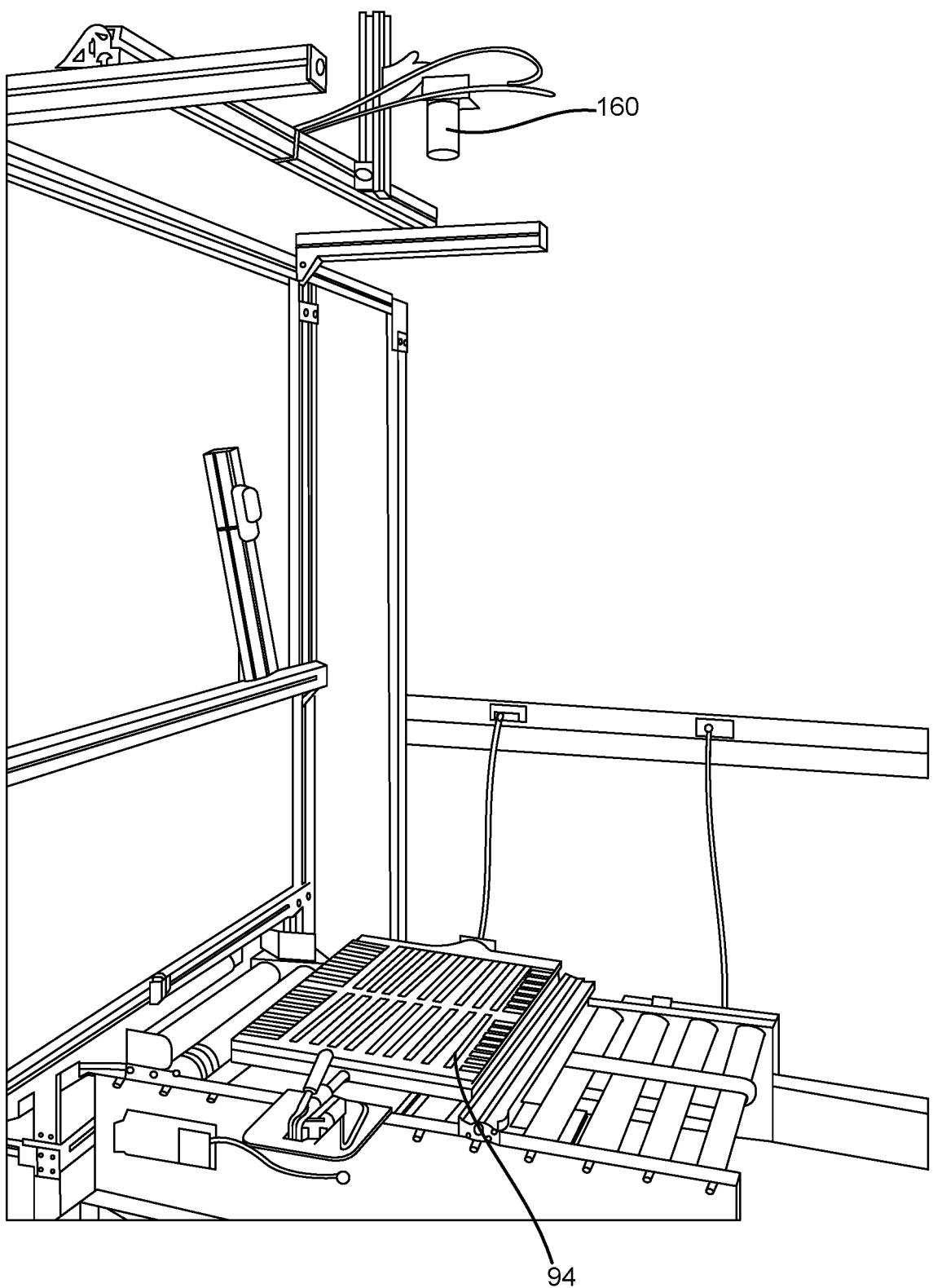
FIG. 37 is an image of a camera mounted above the template.

Referring to FIG. 37, the analysis (e.g., imaging) system 160 captures and processes a digital image of the planted, lighted template 94 before the robot releases the seeds onto the planting media. The imaging system 160 (e.g., camera) can be mounted directly above the backlit template 94, as positioned by the power system. Appropriate software can then execute a blob detection tool and counting algorithm to assess the total number of seeds planted.

Figure 11A:
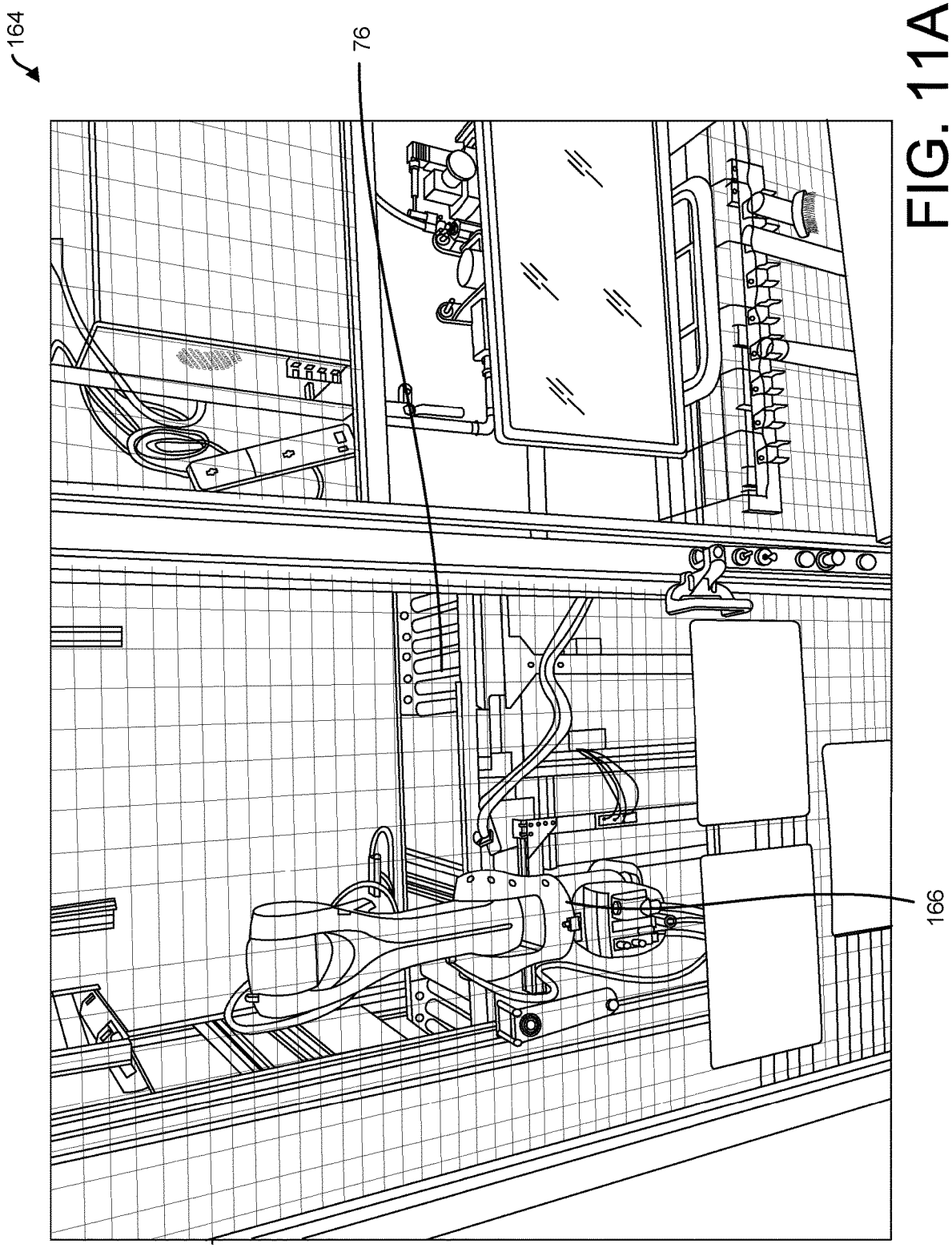
FIG. 11A is an image of a planting verification and correction station.
Figure 11B:
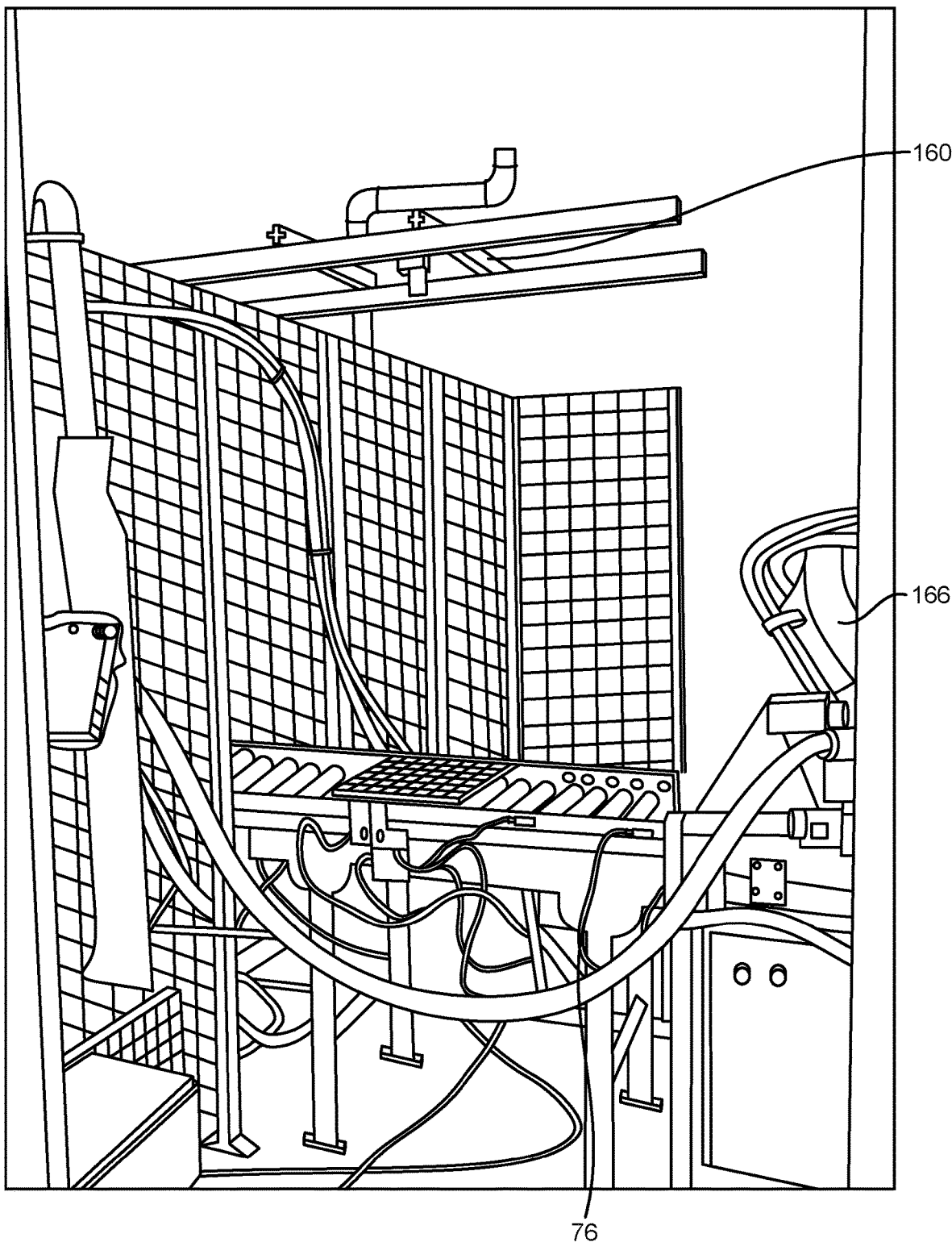
FIG. 11B is a second perspective of a planting verification and correction station.

Referring to FIGS. 11A and 11B, the trays 70, 72 with the seeds planted thereon are conveyed by the tray conveyor 76 to a planting verification and correction station 164. The tray ID is read by a sensor and communicated to the controller. The Tray Table in the database is inputted to the controller to determine the proper seed count for the tray 70, 72. The tray 70, 72 is imaged with an imaging system 160, including a camera and proper lighting. For example, when imaging an RET tray 72, the tray 72 may be backlit. When imaging a WG tray 70, lighting from above may be used. The images are inputted to a controller (e.g., a standalone computer) and analyzed using imaging software to determine, for example, coordinates of empty spaces (e.g., spaces on the tray free from seed) and number of seeds on the tray. The software may also determine if there is debris or other foreign material that is not a seed, the physical purity of the planted seed, the variety of planted seed, any damaged seeds, and other characteristics. This seed information is communicated to the system controller. Using this information, the controller communicates with a seed-adjustment robot 166 to adjust the amount of seeds on the tray 70, 72 and/or remove debris/foreign material, damaged, impure, or incorrect seeds from the tray 70, 72. If the tray 70, 72 has too many seeds as determined by the controller based on information from the Tray Table in the database or detected debris, then the controller communicates with the seed-adjustment robot 166 to remove one or more seeds from the tray 70, 72 and/or remove the detected debris/foreign material, damaged, impure, or incorrect seeds from the tray.

If the controller determines that one or more seeds are missing from the tray 70, 72, then the controller communicates with the seed-adjustment robot 166 to add one or more seeds to the tray 70, 72 from a seed correction area 164. In some embodiments, it is preferable to add too many seeds and remove seed as necessary. In alternative embodiments, it is preferable to add too little seed and add seed as necessary. The supply of correction seeds at the seed correction area is a sub set of the seeds deposited at the cylinder seeder 86. These seeds are pneumatically conveyed to the correction area 164 where they are singulated and positioned in an apparatus for the seed-correction robot 166 to access as needed. The apparatus can generally comprise a pick point apparatus, a vacuum (e.g., a vacuum nozzle), etc. The seeds are automatically replaced as the seed-correction robot 166 removes them from the apparatus. After all trays 70, 72 are processed from that group, the extra seeds are pneumatically removed from the system and the next batch of correction seeds is loaded.

In one or more embodiments, additional or alternate imaging may be used. For example, sensors such as but not limited to hyperspectral, volumetric, X-ray may be used. Imaging like this could also be used to sort seed, removing the deviant seeds and eliminating the need for a quality test as the seed lot has already been screened and sorted by genetic imaging profile. The collection of hyperspectral/near-infrared (NIR) imaging data on seed at the point of planting for germination/RET tests and/or at the evaluation point for the same tests could be used to estimate a seed lots varietal and trait purity thus completing two quality test requirements from the same sample.

Figure 12:
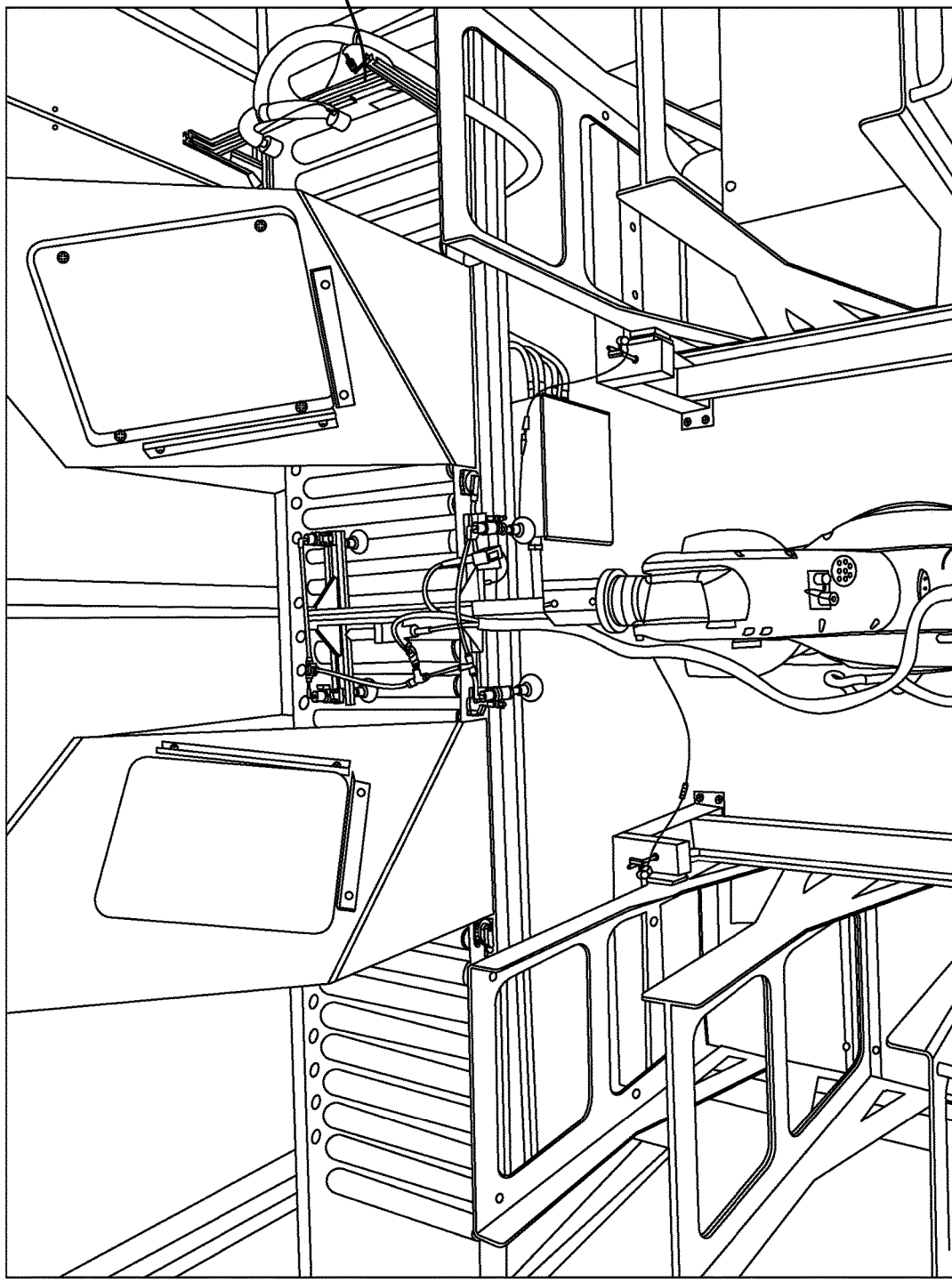
FIG. 12 is an image of a lid placing and tamping station.

Referring to FIG. 12, after validating the seed planting, the trays are conveyed to a lid and tamping station 168 along the tray conveyor 76. The RET trays 72 require a plastic lid before being placed in the germination chambers. A robot 170 places the lids on the RET trays 72. The WG trays 70 require tamping of the seeds. The same robot 170 (or a different robot) tamps the seeds down into the damp towels by means of a plastic plate. The controller controls the operation of the robot 170 and determines which tray 70, 72 needs which process by receiving the tray ID scanned by a sensor.

Figure 13:
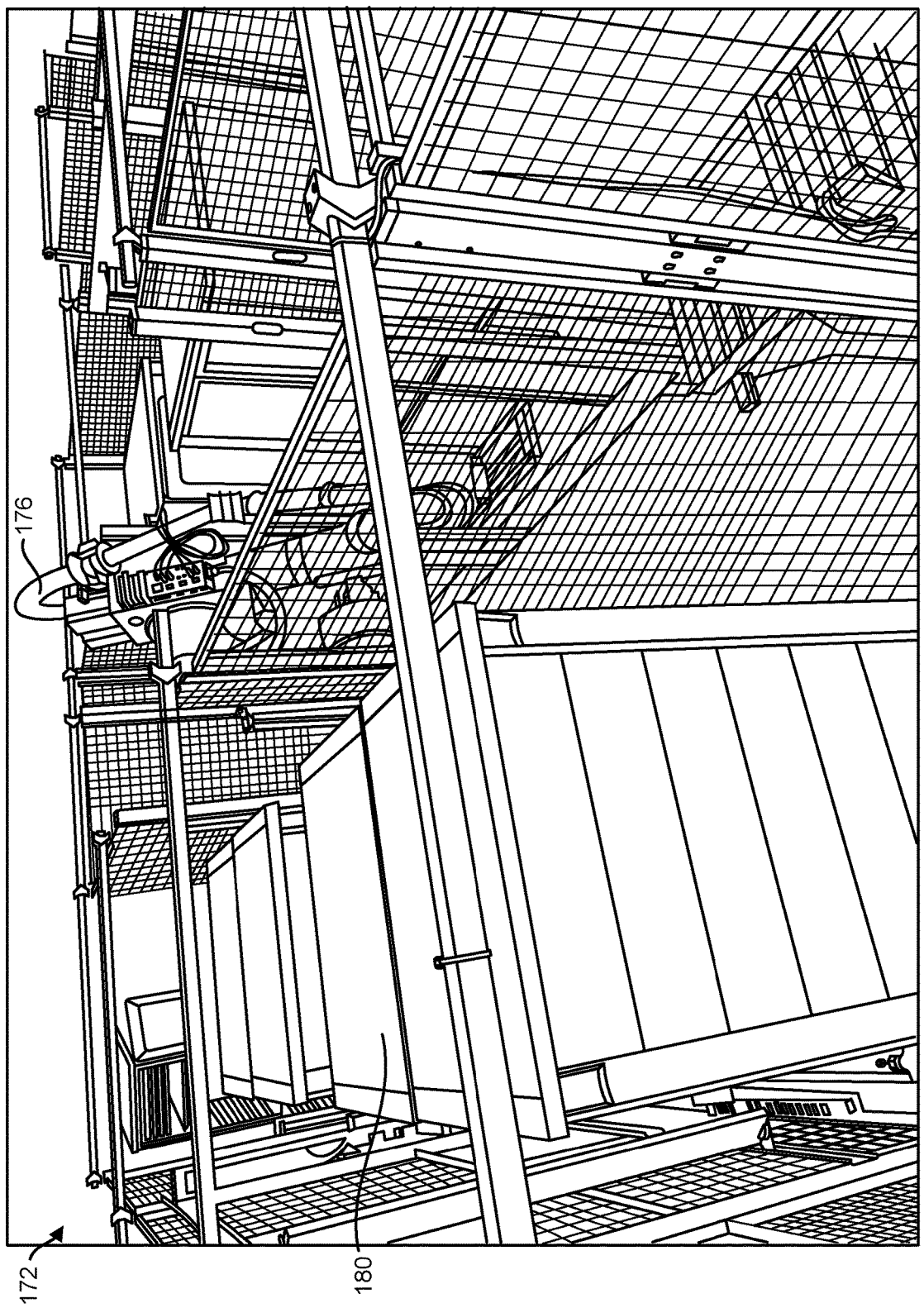
FIG. 13 is an image of a cart-loading station.
Figure 14:
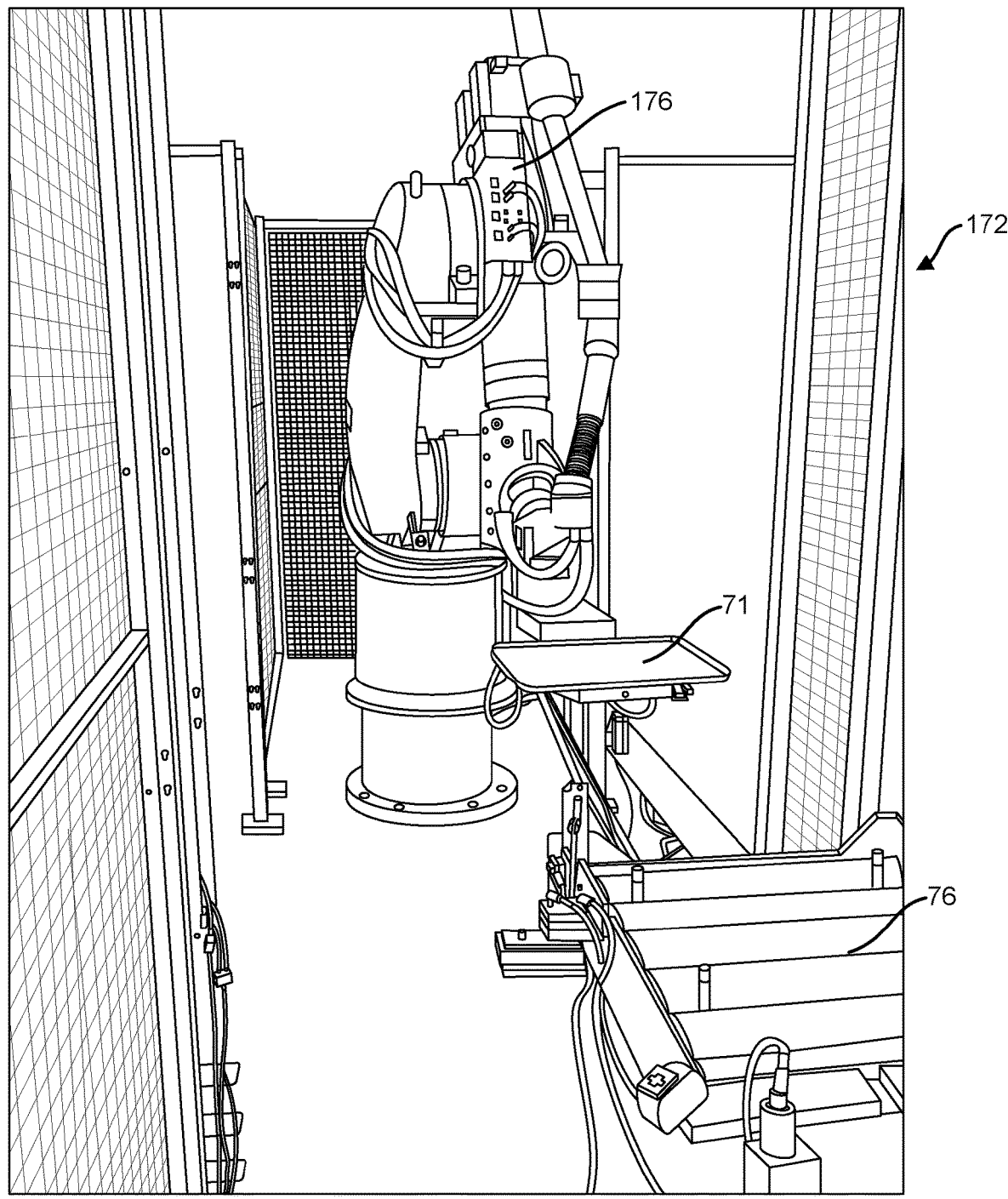
FIG. 14 is an image of a tray loading robot.

Referring to FIGS. 13 and 14, after lids are placed for RET trays 72 or tamping is completed for WG trays 70, the trays 70, 72 are conveyed via the tray conveyor 76 to a cart-loading station 172. The cart-loading station 172 includes a tray-loading robot 176 and a cart loading area. The tray-loading robot 176 removes the trays 70, 72 from the tray conveyor 76 and loads the trays 70, 72 into lighted germination carts 180 in the cart loading area. The carts 180 are loaded into a receiving zone of the cart loading area manually although the carts may be loaded by a robot 176 or other machine. An ID tag on the cart (e.g., barcode or RFID) is scanned and added to the database. A cart indexer moves the carts automatically from the receiving zone, through a loading zone and into an exit zone. At the loading zone, the robot finds the center line of the carts and adjusts the insert points based on laser measuring sensors. As trays 70, 72 of test seed arrive into the area they are picked by the robot 176 and positioned into the appropriate cart. Once the carts 180 are loaded to the appropriate quantity they are moved to the exit zone where an operator takes the cart 180 to an assigned germination room 184. New carts 180 are loaded into the receiving zone each time a pair of carts 180 are removed. This allows the automation line to run without interruption.

Figure 15:
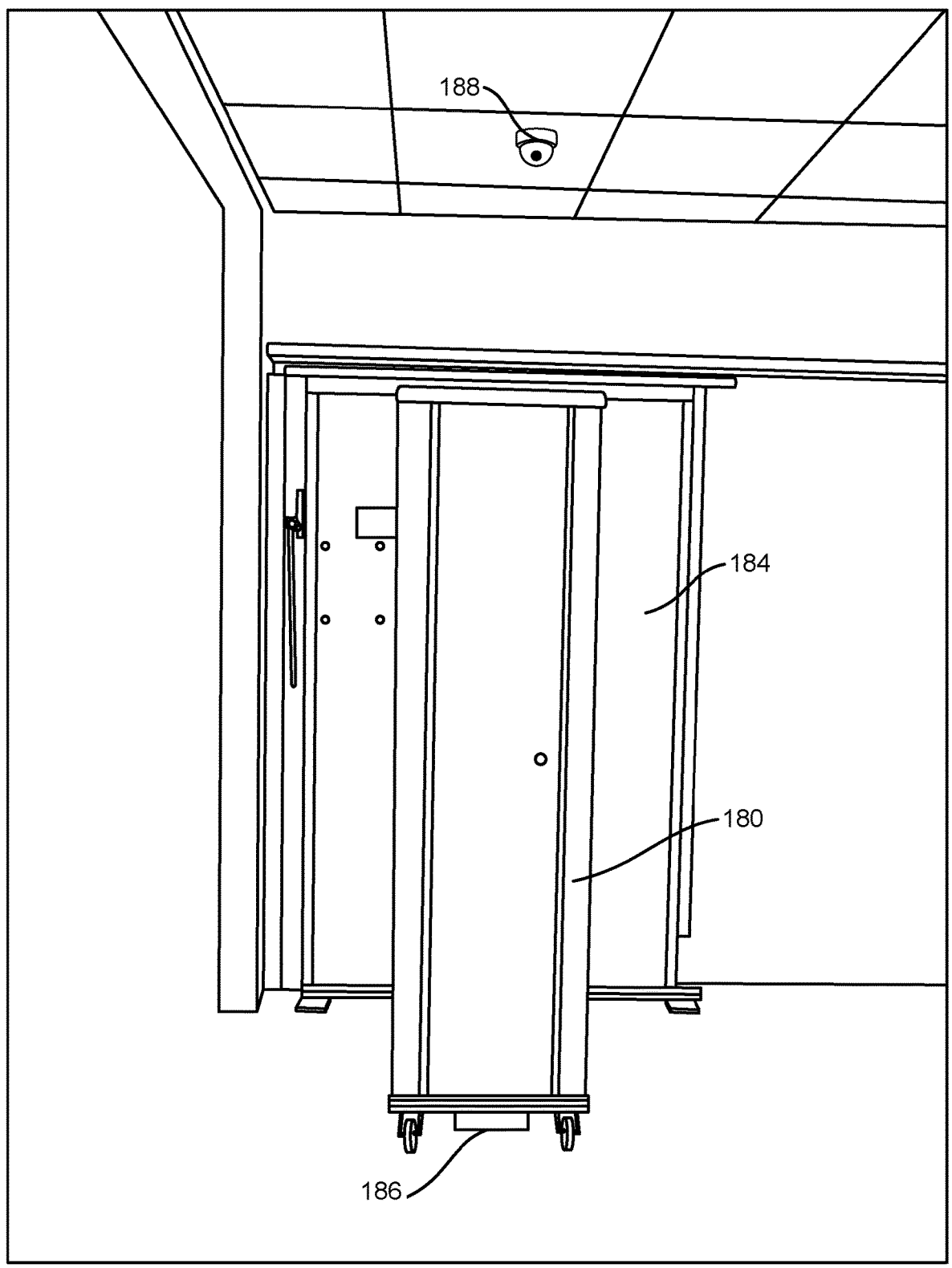
FIG. 15 is an image of a cart at the entrance to a germination room.

Referring to FIG. 15, prior to the carts 180 entering the germination rooms 184, they are placed within a section 186 of the entry door and scanned for proper ID tag reading to ensure that the correct test is being performed on the system. This process can take place automatically and/or manually. A green light 188 will indicate that the ID tag matches the system and the cart 180 will be allowed into the room. A negative ID tag reading will result in a warning light 188 indicating a discrepancy in the process.

Figure 16:
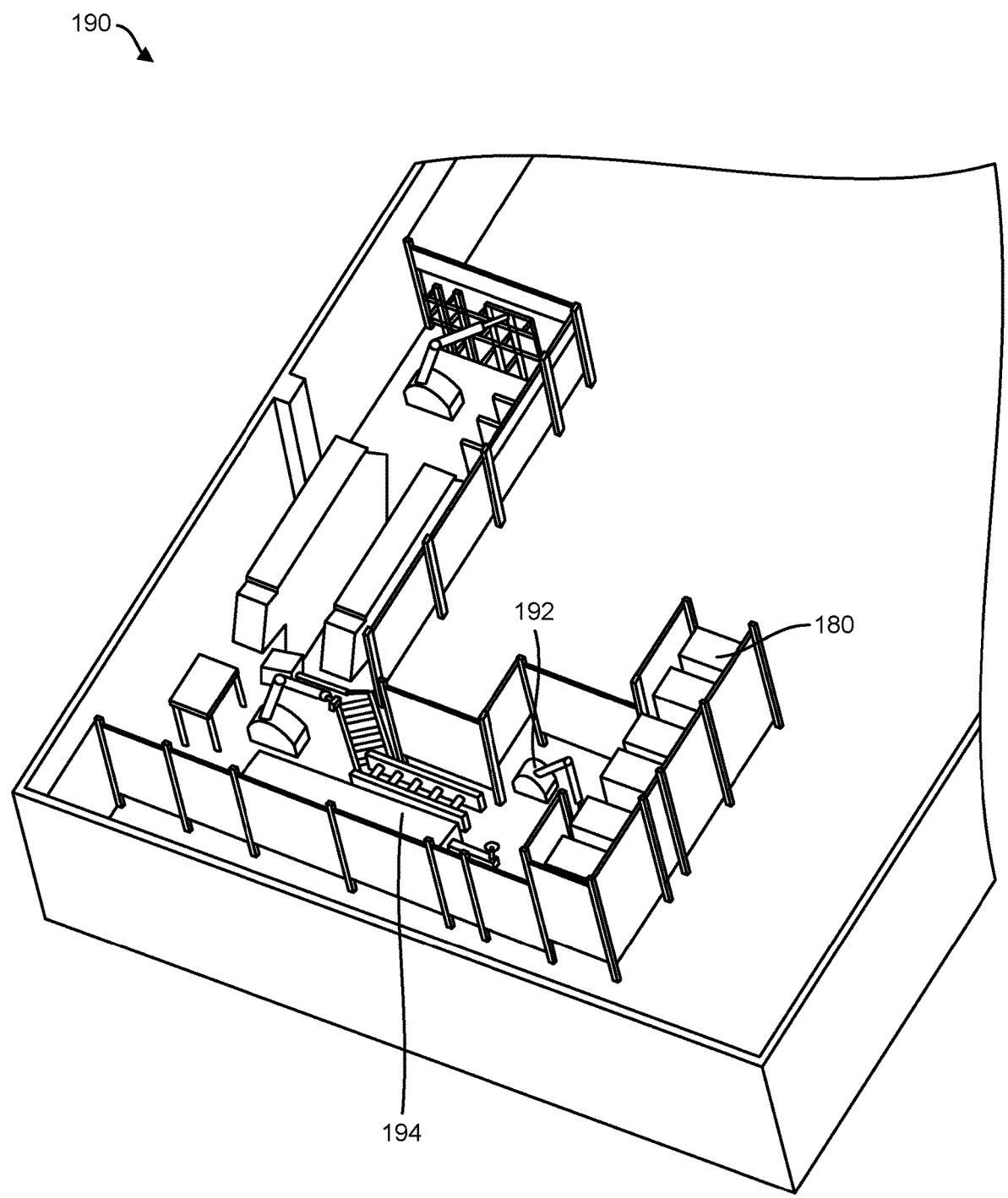
FIG. 16 is an image of an analysis and evaluation station.

Referring to FIG. 16, after the allotted amount of days when the samples have sprouted, the RET carts 180 are removed from the germination room 184 and placed into the Analysis and Evaluation station 190 of the system. In the illustrated embodiment, the analysis performed at the Analysis and Evaluation station 190 is based on seed imaging. In one or more embodiments, one or more other types of analyses of the seeds, in addition to or in place of imaging, may be used to analyze and evaluate the seeds. In one embodiment, the following occurs at the Analysis and Evaluation station 190 (the WG trays are evaluated automatically and/or manually in a separate area):

(i) The carts are placed in an Analysis and Evaluation cart indexer which holds a total of six carts at any given time.

(ii) The imaging robot (or human) 192 will scan the ID code on the carts 180 to ensure the correct test data is being recorded and then will remove the trays 70, 72 from the carts 180 and place them into the imaging station 194. The removal of trays 70, 72 occurs either automatically by a robot or manually.

(iii) The seeds are imaged and data is collected and recorded. The imaging and tracking of information takes place through machine-readable tags (e.g., RFID tags). In some embodiments, imaging systems are placed over a conveyor belt in the imaging station and the trays are placed on the conveyor belt. As the conveyor belt moves, the various trays are processed through the imaging station in either a static or continuous manner. Alternatively, the imaging can occur by simply moving trays in and out of the imaging station without a conveyor belt. The analysis conducted in this process can comprise at least one of radicle emergence testing, warm germ testing, emergence testing, appearance testing, morphology testing, or a combination thereof.

(iv) Once the seeds are imaged and the data is recorded a tray washing placement robot 196 (or human) will be signaled to remove the tray 70, 72 from the imager 194 and place it on a location of the dishwasher 196 where it is then conveyed down the line, the agar and seeds are stripped off of the tray and is then sent through the dishwashing conveyor.

(v) Once the tray has been washed through the dishwasher, the clean tray placement robot 198 (or human)

will remove the tray from the dishwasher and place it into the clean cart tray to be reused.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method for automated seed planting and analysis, the method comprising:
   conveying containers containing seeds to an automated seed planting station, wherein each container includes a machine-readable tag configured to associate the container with information stored in a database relating to the seeds contained in the container;
   selecting a planting tray to receive the seeds at the automated seed planting station, from multiple different types of planting trays, based on a test type for the seeds to be planted in the selected planting tray, wherein the different types of planting trays include radicle emergence testing (RET) trays and warm germ (WG) testing trays, and wherein the selected planting tray includes a first planting media corresponding to the test type for the seeds to be planted in the selected planting tray, and wherein at least one of the different types of planting trays includes a second planting media different from the first planting media;
   planting at least some of the seeds from the containers onto the selected planting tray using the seed planting station, wherein the selected planting tray includes a machine-readable tag configured to associate the planting tray with the information stored in the database relating to the seeds planted on the planting tray;
   transporting the seeds on the selected planting tray to a germination area;
   germinating at least one of the seeds on the planting tray at the germination area; and then
   after the planting tray is at the germination area for at least a defined amount of time, transporting the seeds on the planting tray to an analysis and evaluation station; and
   analyzing the germinated seed(s) on the planting tray at the analysis and evaluation station, consistent with the test type for the seeds.

2. The method of claim 1, further comprising tracking the containers during said conveying by scanning the machine-readable tags at discrete locations during said conveying.

3. The method of claim 1, wherein said planting comprises removing the seeds from the containers, placing the seeds in an automated seeder of the seed planting station, and planting the seeds using the automated seeder.

4. The method of claim 3, further comprising pairing, using a processor having access to the database, seeds from one of the containers with seeds of another one of the containers to form plantable pairs of seeds to be planted on the same planting tray.

5. The method of claim 4, wherein selecting the type of planting tray to receive the seeds includes:
   determining, using the processor, the type of planting tray required for the analyzing by scanning the machine-readable tags located on the containers; and
   automatically providing the correct type of planting tray from a tray holding area.

6. The method of claim 5, further comprising confirming, using the processor, that the correct type of planting tray for a selected container of seeds is provided by scanning the machine-readable tag located on the planting tray.

7. The method of claim 1, further comprising analyzing the tray after said planting and before germination to determine one or more of: the number of seeds planted on the planting tray, the variety of seeds planted on the planting tray, the presence of foreign material on the planting tray, the physical purity of seeds planted on the planting tray, the presence of damaged seeds planted on the planting tray, and a combination thereof.

8. The method of claim 1, further comprising scanning the machine-readable tag of the planting tray after said planting and prior to said germinating.

9. The method of claim 1, wherein said analyzing comprises conducting at least one of radicle emergence testing, warm germ testing, emergence testing, appearance testing, morphology testing, or a combination thereof.

10. The method of claim 1, further comprising placing a template on the planting tray prior to said planting, using an automated device.

11. The method of claim 10, wherein the template comprises a backlit template.

12. The method of claim 10, wherein planting at least some of the seeds from the containers onto the selected planting tray includes:
   positioning the template in a placement configuration in which wells of an upper portion of the template are not aligned with openings of a bottom portion of the template;
   positioning at least some of the seeds from the containers in the wells of the upper portion of the template; and
   moving the template from the placement configuration to a delivery configuration in which the wells of the upper portion of the template are aligned with the openings of the bottom portion of the template, to thereby allow the seeds in the wells of the upper portion of the template to fall through the openings of the bottom portion of the template and onto the planting tray over which the template is positioned.

13. The method of claim 1, wherein the first planting media is selected from a paper substrate and/or an agar fluid.

14. The method of claim 1, further comprising placing the first planting media on the selected planting tray.

15. A method for automated seed planting and analysis, the method comprising:
   conveying containers containing seeds to an automated seed planting station;
   selecting a planting tray to receive the seeds at the automated seed planting station, from multiple different types of planting trays, based on a test type for the seeds to be planted in the selected planting tray, wherein the selected planting tray includes a first planting media corresponding to the test type for the seeds to be planted in the selected planting tray, and wherein at least one of the different types of planting trays includes a second planting media different from the first planting media;
   transporting the selected planting tray to a temperature control system;

activating the temperature control system, based on a type of the first planting media included on the selected planting tray; and then placing a template on the selected planting tray using an automated device;

planting at least some of the seeds from the containers onto the selected planting tray through the template using the seed planting station;

transporting the seeds on the selected planting tray to a germination area;

transporting the seeds on the planting tray from the germination area to an analysis and evaluation station; and analyzing the seeds on the planting tray at the analysis and evaluation station, consistent with the test type for the seeds.

16. The method of claim 15, wherein planting at least some of the seeds from the containers onto the selected planting tray includes:

positioning the template in a placement configuration in which wells of an upper portion of the template are not aligned with openings of a bottom portion of the template;

positioning at least some of the seeds from the containers in the wells of the upper portion of the template; and moving the template from the placement configuration to a delivery configuration in which the wells of the upper portion of the template are aligned with the openings of the bottom portion of the template, to thereby allow the seeds in the wells of the upper portion of the template to fall through the openings of the bottom portion of the template and onto the planting tray over which the template is positioned.

17. The method of claim 15, wherein the different types of planting trays include radicle emergence testing (RET) trays and warm germ (WG) testing trays; and wherein the first planting media is selected from a paper substrate and/or an agar fluid.

18. The method of claim 15, further comprising placing the first planting media on the selected planting tray.

* * * * *